(12) United States Patent
Banz et al.

(10) Patent No.: US 6,592,910 B1
(45) Date of Patent: Jul. 15, 2003

(54) METHODS OF TREATING CLINICAL DISEASES WITH ISOFLAVONES

(75) Inventors: William J. Banz, Creal Springs, IL (US); Michael R. Peluso, Makanda, IL (US); Todd A. Winters, Murphysboro, IL (US); Michael F. Shanahan, Carbondale, IL (US)

(73) Assignee: Board of Trustees, Southern Illinois University, Carbondale, IL (US)

( * ) Notice: Subject to any disclaimer, the term of this patent is extended or adjusted under 35 U.S.C. 154(b) by 0 days.

(21) Appl. No.: 09/553,017

(22) Filed: Apr. 20, 2000

Related U.S. Application Data

(60) Provisional application No. 60/130,156, filed on Apr. 20, 1999.

(51) Int. Cl.[7] .............................................. A61K 35/78
(52) U.S. Cl. ..................... 424/757; 424/725; 514/893
(58) Field of Search ................................ 424/725, 757; 514/893

(56) References Cited

U.S. PATENT DOCUMENTS

| | | | |
|---|---|---|---|
| 4,263,286 A | * | 4/1981 | Nakajima et al. |
| 4,428,876 A | * | 1/1984 | Iwamura |
| 4,524,067 A | * | 6/1985 | Arichi et al. |
| 4,557,927 A | * | 12/1985 | Miyake et al. |
| 5,830,887 A | | 11/1998 | Kelly ........................... 514/182 |
| 5,855,892 A | | 1/1999 | Potter et al. .............. 424/195.1 |
| 5,885,632 A | * | 3/1999 | Takebe et al. |
| 6,180,139 B1 | * | 1/2001 | Hsia et al. |

FOREIGN PATENT DOCUMENTS

| | | |
|---|---|---|
| CN | 1123115 | * 11/1994 |
| EP | 0 943 245 A | 9/1999 |
| WO | 9516362 | * 8/1995 |
| WO | WO 98/03084 | 1/1998 |
| WO | WO 00/030663 | 6/2000 |
| WO | WO 00/030664 | 6/2000 |
| WO | WO 00/030665 | 6/2000 |

OTHER PUBLICATIONS

Horii et al. Daizu Tanpakushitsu Eiyo Kenkyukai Kaishi. vol. 4, No. 1, pp. 69–74, 1983.*
DiFrancesco et al. Acta Cardiologica. vol. 45, No. 4, pp. 257–271, 1990.*
Whitehead et al. Res. Vet. Sci. vol. 21, No. 2, pp. 141–145, 1976.*
Niiho et al. Yakugaku Zasshi. J. Pharm. Soc. Japan. vol. 110, No. 8, pp. 604–611, abstract, 1990.*
Kendall, T. Living + : Lipids and lifestyle, 3 pages from website www.bcpwa.org, 1996.*
Banz, W. et al., "The Effects of Soy Protein and Isoflavones on Platelet, Lipid and Liver Measurements in Zucker Rats," FASEB J. 13:A885 (Mar. 1999).
Banz, W. et al., "High Isoflavone Soy Protein Ameliorates Impaired Glucose Tolerance and Fatty Liver in Female Zucker Obese Rats," FASEB J. 14:A765 (Mar. 2000).
Jonas, J.C. et al., "Multiple effects and stimulation of insulin secretion by the tyronsine kinase inhibitor genistein in normal mouse islets," Brit. J. Pharmacol. 114:872–880 (1995).
Keizo, S., "Composition for Promoting Differentiation of Cell Into Fat Cell," Patent Abstracts of Japan, Publication No. 10101561 (Apr. 1998).
Nogowski, L. et al., "Genistein–Induced Changes in Lipid Metabolism of Ovariectomized Rats," Ann. Nutr. Met. 42:360–366 (Dec. 1998).
Schoene, N.W. and Guidry, C.A., "Dietary soy isoflavaones inhibit activation of rat platelets," J. Nutr. Biochem. 10:421–426 (Jul. 1999).
Database WPI, Accession No. 1998–011907, Derwent WPI English language abstract for JP 09 255570 A.
International Search Report for International Application No. PCT/US00/10543, mailed Oct. 5, 2000.
Allain, C.C., et al., "Enzymatic Determination of Total Serum Cholesterol," Clin. Chem. 20:470–475 (1974).
Anderson, J.W., et al., "Meta–Analysis of the Effects of Soy Protein Intake on Serum Lipids," N. Engl. J. Med. 333:276–282 (1995).
Anthony, M.S., et al., "Effects of Soy Isoflavones on Atherosclerosis: Potential Mechanisms," Am. J. Clin. Nutr. 68:1390S–1393S (Dec. 1998).
Anthony, M.S., et al., "Soy Protein Versus Soy Phytoestrogens in the Prevention of Diet–Induced Coronary Artery Atherosclerosis of Male Cynomolgus Monkeys," Arterioscler. Thromb. Vasc. Biol. 17:2524–2531 (1997).
Baker, W., et al., "Synthetical Experiments in the isoFlavone Group. Part III. A Synthesis of Genistein," J. Chem. Soc. p. 3115–3118 (1928).
Baker, W., et al., "Synthetical Experiments in the isoflavone Group. Part VII. Synthesis of Daidzein," J. Chem. Soc. p. 274–275 (1933).
Baker, W., et al., "A New Synthesis of isoFlavones," Nature 169:706 (1952).
Baker, W., et al., "A New Synthesis of isoFlavones. Part I," J. Chem. Soc. p. 1852–1860 (1953).

(List continued on next page.)

Primary Examiner—Christopher R. Tate
(74) Attorney, Agent, or Firm—Sterne, Kessler, Goldstein & Fox PLLC

(57) ABSTRACT

The present invention provides a method of treating or preventing certain medical conditions with isoflavones. More specifically, the invention provides a method of treating or preventing one or more of the following medical conditions: hepatic steatosis, steatohepatitis, insulin resistance, impaired glucose tolerance, syndrome X, abnormal platelet function, or abnormal vascular reactivity, with compositions containing isoflavones.

29 Claims, 14 Drawing Sheets

OTHER PUBLICATIONS

Bradbury, R.B., et al. "The Chemistry of Subterranean Clover. Part I. Isolation of Formononetin and Genistein," *J. Chem. Soc.* p. 3447–3449 (1951).

Carroll, K.K., and Kurowska, E.M., "Soy Consumption and Cholesterol Reduction: Review of Animal and Human Studies," *J. Nutr.* 125:594S–597S (1995).

Després, J.-P., et al., "Regional Distribution of Body Fat, Plasma Lipoproteins, and Cardiovascular Disease," *Arteriosclerosis* 10:497–511 (1990).

Fletcher, M.J., "A Colorimetric Method for Estimating Serum Triglycerides," *Clin. Chim. Acta* 22:393–397 (1968).

Folch, J., et al., "A Simple Method for the Isolation and Purification of Total Lipides from Animal Tissues," *J. Biol. Chem.* 226:497–509 (1957).

Fukuda, N., et al., "Altered Hepatic Metabolism of Free Fatty Acids Underlying Hypersecretion of Very Low Density Lipoproteins in the Genetically Obese Zucker Rat," *J. Biol. Chem.* 257:14066–14072 (1982).

Ganguly, A.K., and Sarre, O.Z., "Genistein and daidzein, metabolites of *Micromonospora halophytica*," *Chem Ind.* 6:201 (1970).

Hayes, K.C., and Pronczuk, A., "Sensitivity to platelet aggregation appears related to the lipoprotein profile and atherosclerosis risk in humans and across species," *Comp. Biochem. Physiol. Biochem. Mol. Biol.* 113B:349–353 (1996).

Honoré, E.K., et al., "Soy isoFlavones enhance coronary vascular reactivity in atherosclerotic female macaques," *Fertil. Steril.* 67:148–154 (1997).

Kagal, S.A., et al., "A Synthesis of isoflavones by a modified Vilsmeier–Haack reaction," *Tetrahedron Letters,* 14:593–597 (1962).

Kasiske, B.L., et al., "The Zucker Rat Model of Obesity, Insulin Resistance, Hyperlipidemia, and Renal Injury," *Hypertension (Suppl. 1)* 19:I–100–I–115 (1992).

Krief, S., and Bazin, R., "Genetic Obesity:Is the Defect in the Sympathetic Nervous System? A Review Through Developmental Studies in the Preobese Zucker Rat," *Proc. Soc. Exp. Biol. Med.* 198:528–538 (1991).

Liao, W., et al., "Lipoprotein Metabolism in the Fat Zucker Rat: Reduced Basal Expression but Normal Regulation of Hepatic Low Density Lipoprotein Receptors," *Endocrinology* 138:3276–3282 (1997).

Lin, R.C., "Serum Cholesterol, Lecithin–Cholesterol Acyltransferase, and Hepatic Hydroxymethylglutaryl Coenzyme A Reductase Activities of Lean and Obese Zucker Rats," *Metabolism* 34:19–24 (1985).

Lowry, O.H., et al., "Protein Measurement with the Folin Phenol reagent," *J. Biol. Chem.* 193:265–275 (1951).

Mahal, H.S., et al., "Synthetical Experiments in the Chromone Group. Part XV. A Synthesis of Formononetin, Daidzein, and ψ–Baptigenin," J. Chem. Soc. p. 1769–1771 (1934).

McNamara, D.J., "Cholesterol Homeostasis in Lean and Obese Male Zucker Rats," *Metabolism* 34:130–135 (1985).

Miller, N.E., et al., "Relation of angiographically defined coronary artery disease to plasma lipoprotein subfractions and apolipoproteins," *Br. Med. J. (Clin. Res. Ed.)* 282:1741–1744 (1981).

Narasimhachari, et al., "Synthetic Experiments in the Benzopyrone Series: Part XXXV—Use of Methyl Formate in IsoFlavone Condensation: Isolation of 2–Hydroxy IsoFlavones," *J. Sci. Industr. Res.* 12B:287–293 (1953).

Nestel, P.J., et al., "Soy Isoflavones Improve Systemic Arterial Compliance but Not Plasma Lipids in Menopausal and Perimenopausal Women," *Arterioscler. Thromb. Vasc. Biol.* 17:3392–3398 (1997).

Nityanand, S., et al., "Kinetics of Serotonin in Platelets in Essential Hypertesion," *Life Sci.* 46:367–372 (1990).

Pope, G.S., et al., "Isolation of an Oestrogenic Isoflavone (Biochanin A) From Red Clover," *Chem. and Industr.* (London) p. 1092 (1953).

Potter, S.M., "Soy Protein and Cardiovascular Disease: the Impact of Bioactive Components in Soy," *Nutr. Rev.* 56:231–235 (Aug. 1998).

Ross, R., et al., "The role of endothelial injury and platelet and macrophage interactions in atherosclerosis," *Circulation (Suppl III)* 70:77–82 (1984).

Ross, R., "The Pathogenesis of Atherosclerosis—An Update," *N. Engl. J. Med.* 314:488–500 (1986).

Sirtori, C.R., et al., "Soy and Cholesterol Reduction: Clinical Experience," *J. Nutr.* 125:598S–605S (1995).

Sirtori, C.R., et al., "Soybean–Protein Diet in the Treatment of Type–II Hyperlipoproteinemia," *Lancet* 1:275–277 (1977).

Sirtori, C.R., et al., "Reduction of serum cholesterol by soy proteins: clinical experience and potential molecular mechanisms," *Nutr. Metab. Cardiovasc. Dis.* 8:334–340 (Oct. 1998).

St. John, L.C., and Bell, F.P., "Arterial lipid biochemistry in the spontaneously hyperlipidemic Zucker rat and its similarity to early atherogenesis," *Atherosclerosis* 86:139–144 (1991).

Surya, I.I., and Akkerman, J.–W.N., "The influence of lipoproteins on blood platelets," *American Heart Journal* 125:272–275 (1993).

Tang, P.M., et al., Expression of Hepatic Microsomal Cholesterol 7α–Hydroxylase Activity in Lean and Obese Zucker Rats, *Biochem. Biophys. Res. Comm.* 150:853–858 (1988).

William, J.K., and Clarkson, T.B., "Dietary soy isoflavones inhibit in–vivo constritor responses of coronary arteries to collagen–induced platelet activation," *Coronary Artery Dis.* 9:759–764 (1998).

Wong E., "Detection and Estimation of Oestrogenic Constituents n Red Clover," *J. Sci. Food Agric.* 13:304–308 (1962).

Yoder, L., et al., "Synthesis of Estrogenic Isoflavone Derivatives," *Proc. Iowa Acad. Sci.* 61:271–277 (1954).

Zemplén, G., et al., "An New Synthesis of Genistein," *Acta. Chim. Hung. Tomus* 19:277–283 (1959). (Abstract).

English language abstract of Zemplén, G., et al. (Document AR15), p. 283.

\* cited by examiner

EFFECT: DIET, C vs LS, $P=0.002$;
C vs HS, $P=0.001$; LS vs HS, NS

EFFECT: DIET, C vs LS, $P=0.1$;
C vs HS, $P=0.003$; LS vs HS, $P=0.1$

*P<0.05 vs CONTROL
N=10 FOR EACH TREATMENT, MEAN±STD. ERROR

N=10 FOR EACH TREATMENT, MEAN±STD. ERROR

*P<0.05 vs CONTROL, **P<0.05 vs GENISTEIN
N=10 FOR EACH TREATMENT, MEAN±STD. ERROR

*P<0.05 vs C, **P<0.05 vs LS
N=10 FOR EACH TREATMENT, MEAN±STD. ERROR

METHODS OF TREATING CLINICAL DISEASES WITH ISOFLAVONES

CROSS-REFERENCE TO RELATED APPLICATIONS

This application claims the benefit of the filing date of U.S. Provisional Application 60/130,156 filed Apr. 20, 1999. The contents of that application are incorporated herein by reference.

BACKGROUND OF THE INVENTION

1. Field of the Invention

The present invention relates, in general, to a method for treating or preventing certain medical clinical conditions with isoflavones. In particular, the present invention relates to a method of treating or preventing one or more of the following medical conditions: hepatic steatosis, steatohepatitis, insulin resistance, impaired glucose tolerance, syndrome X, abnormal platelet function, or abnormal vascular reactivity, with compositions containing isoflavones.

2. Related Art

Dietary soy protein has been shown to be hypocholesterolemic in human and animal studies (Carroll, K. K. and Kurowska, E. M., *J. Nuir.* 125:594S–597S (1995)). In humans, the cholesterol-lowering effect has been observed primarily in persons that are hypercholesterolemic prior to dietary intervention (Anderson, J. W., et al., *N. Engl. J. Med.* 333:276–282 (1995)). Soy protein diets have been particularly beneficial in the treatment of type II hyperlipoproteinemia (Sirtori, C. R., et al., *Lancet* 1:275–277 (1977); Sirtori, C. R., et al., *J. Nutr.* 125:598S–605S (1995)), which is characterized by elevated plasma LDL cholesterol (type IIa) or plasma LDL and VLDL cholesterol and triglyceride (type IIb). Hyperlipidemia is associated with the development of atherosclerosis, cardiovascular disease (CVD), and non-insulin dependent diabetes mellitus (NIDDM) (Despres, J.-P., et al., *Arteriosclerosis* 10:497–51 1 (1990)). Therefore, a hypocholesterolemic effect of soy protein can lower CVD and NIDDM risk.

Hypotheses have been proposed for mechanisms responsible for the cholesterol-lowering effect of soy protein (Anthony, M. S., et al., *Am. J. Clin. Nutr.* 68:1390S–1393S (1998); Potter, S. M., *Nutr. Rev.* 56:231–235 (1998); Sirtori, C. R., et al., *Nutr. Metab. Cardiovasc. Dis.* 8:334–340 (1998)). The soy protein amino acid composition, specific soy peptides and globulins, and the isoflavones and saponins associated with soy protein all have been suggested as factors participating in the hypocholesterolemic response. The liver centrally regulates whole-body cholesterol excretion through the production and secretion of bile. Therefore, a mechanism responsible for the hypocholesterolemic effect of soy protein likely includes normalization of aberrant hepatic cholesterol and bile acid metabolism. The liver also centrally regulates plasma cholesterol and triglyceride concentrations through production, secretion, and catabolism of apolipoprotein B (apoB). Furthermore, visceral obesity and elevated portal-hepatic free fatty acid flux induces hepatic steatosis and elevates the production of triglyceride-rich apoB-lipoproteins (Despres, J.-P., et al., *Arteriosclerosis* 10:497–511 (1990)). Therefore, a mechanism responsible for the hypocholesterolemic effect of soy protein can also include normalization of aberrant hepatic fatty acid and triglyceride metabolism.

Obese (fa/fa) Zucker rats are hyperinsulinemic, hyperlipoproteinemic, and develop hepatic steatosis within a few weeks after birth (Krief, S. and Bazin, R., *Proc. Soc. Exp. Biol. Med.* 198:528–538 (1991)). This rat can be used as a model system for symptoms associated with the development of CVD and NIDDM (St. John, L. C. and Bell, F. P., *Atherosclerosis* 86:139–144 (1991); Kasiske, B. L., et al., *Hypertension (Suppl.* 1) 19:1110–1115 (1992)). Markedly elevated pancreatic insulin secretion suppresses hepatic fatty acid catabolism and stimulates hepatic lipogenesis and fatty acid esterification. Elevated triglyceride and cholesteryl ester availability up-regulates secretion of apoB-lipoproteins and induces lipid storage in cytosolic droplets (Fukuda, N., et al., *J Biol. Chem.* 257:14066–14072 (1982)). Furthermore, there is an absence of the feeding-induced diurnal rise-and-fall of hepatic cholesterogenesis in adult male obese rats (Lin, R. C., *Metabolism* 34:19–24 (1985)), and fecal neutral sterols are 50% lower in obese rats than in lean rats (McNamara, D. J., *Metabolism* 34:130–135 (1985)). Expression of the hepatic LDL receptor is 60% lower in obese rats than in lean rats, without a difference in LDL receptor mRNA (Liao, W., et al., *Endocrinology* 138:3276–3282 (1997)). The diurnal rhythm of hepatic cholesterol 7α-hydroxylase has also been shown to be absent in obese rats (Tang, P. M., et al., *Biochem. Biophys. Res. Commun.* 150:853–858 (1988)).

Blood platelets also play an integral role in the development of CVD (Ross, R., *N. Engl. J Med.* 314:488–500 (1986)). Arterial cholesterol deposition and blood platelet sensitivity are elevated by plasma LDL and lowered by plasma HDL (Miller, N. E., et al., *Clin. Res.* 282:1741–1744 (1981), Surya, I. I. and Akkerman, W. N., *Heart J.* 125:272–275 (1993)). The variation in platelet sensitivity found among species has been shown to correlate directly with susceptibility of the species to CVD (Hayes, K. C. and Pronczuk, A., *Comp. Biochem. Physiol.* 11313:349–353 (1996)). Furthermore, the plasma LDL cholesterol-to-HDL cholesterol ratio has been found to vary directly with platelet sensitivity both across and within species. Platelet activation is accompanied by release of compounds from intraplatelet granules that promote atherosclerotic lesion formation (Ross, R., et al., *Circulation (Suppl* III) 70:77–82 (1984)). For example, platelet-derived growth factor stimulates vascular smooth muscle cell migration and proliferation in the arterial intima. Activated platelets also release 5-hydroxytryptamine (5HT), commonly known as serotonin, which plays a role in the pathophysiology of essential hypertension (Nityanand, S., et al., *Life Sci.* 46:367–372 (1990)). Dietary soy protein rich in isoflavones has been shown to reduce atherosclerotic lesion development in male cynomolgus monkeys fed an atherogenic diet (Anthony, M. S., et al., *Arterioscler. Thromb. Vasc. Biol.* 17:2524–2531 (1997)). An inhibitory effect of isoflavone-rich soy protein on platelet aggregability has been reported in female rhesus monkeys (Williams, J. K. and Clarkson, T. B., *Coronary Artery Dis.* 9:759–764 (1998)). These effects of isoflavone-rich soy protein can result in part from a reduction in the plasma LDL cholesterol-to-HDL cholesterol ratio. Another study has shown rapid inhibition of vasoconstriction in stenotic arteries of female macaques after intravenous infusion of the soy isoflavone genistein (Honore, E. K., el al., *Fertil. Steril.* 67:148–154 (1997)). Improved systemic arterial compliance has also been shown after dietary isoflavone supplementation in menopausal women (Nestel, P. J., et al., *Axterioscler. Thromb. Vase. Biol.* 17:3392–3398 (1997)).

SUMMARY OF THE INVENTION

The present invention provides a method of preventing or treating the symptoms of one or more of the following clinical medical conditions: hepatic steatosis, steatohepatitis, insulin resistance, impaired glucose tolerance, syndrome X, abnormal platelet function, or abnormal vascular reactivity. This method comprises administering to a subject having, or predisposed to, one or more of these conditions, a therapeutically effective amount of at least one isoflavonoid.

The present invention further provides a method of preventing or treating the symptoms of one or more of the aforementioned clinical medical conditions by administering to a subject having, or predisposed to, one or more of these conditions, a therapeutically effective amount of at least one isoflavonoid in combination with soy protein.

The present invention also provides a method of preventing or treating the symptoms of one or more of the aforementioned clinical medical conditions by administering to a subject having, or predisposed to, one or more of these conditions, a therapeutically effective amount of at least one isoflavonoid in combination with dietary ingredients or supplements other than soy protein.

The present invention further provides a method of preventing or treating the symptoms of one or more of the aforementioned clinical medical conditions by administering to a subject having, or predisposed to, one or more of these conditions, a therapeutically effective amount of at least one isoflavonoid which is contained in an isoflavone-enriched fraction of soy protein.

The present invention also provides a method of preventing or treating the symptoms of one or more of the aforementioned clinical medical conditions by administering to a subject having, or predisposed to, one or more of these conditions, a therapeutically effective amount of at least one isoflavonoid which is contained in an isoflavone-enriched fraction of soy protein in combination with soy protein.

The present invention further provides a method of preventing or treating the symptoms of one or more of the aforementioned clinical medical conditions by administering to a subject having, or predisposed to, one or more of these conditions, a therapeutically effective amount of at least one isoflavonoid which is contained in an isoflavone-enriched fraction of soy protein in combination with dietary ingredients or supplements other than soy protein.

Further objects, advantages, and novel features of the present invention will become apparent from the following detailed description of the invention.

DETAILED DESCRIPTION OF THE PREFERRED EMBODIMENTS

Figure 1A:
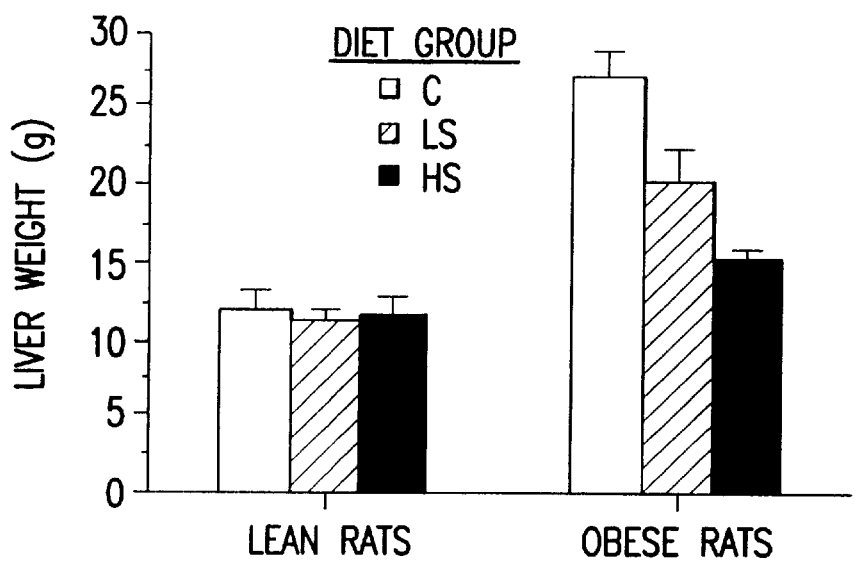
FIGS. 1A–F show a series of bar graphs depicting liver cholesterol and triglyceride concentrations in male lean and obese Zucker rats fed casein (C), isoflavone-poor soy protein (LS), or isoflavone-rich (HS) soy protein-based diets for 70 days.
Figure 1B:
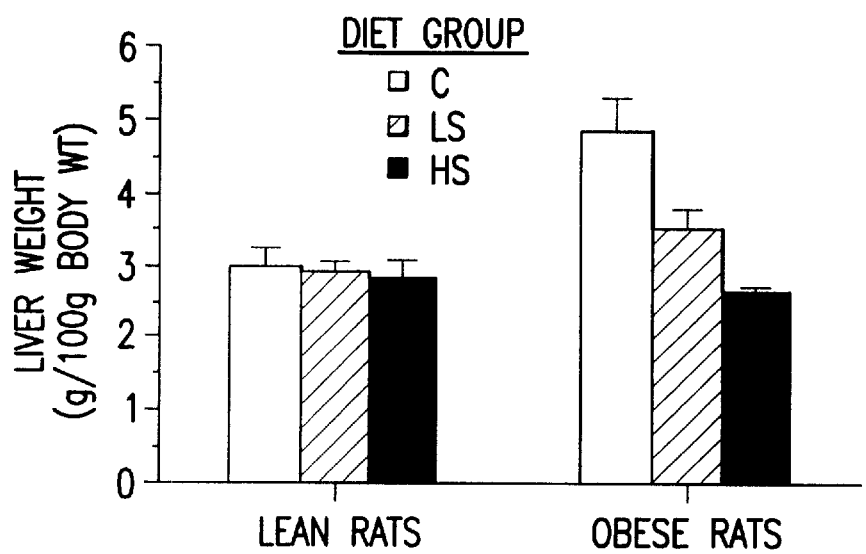
Figure 1C:
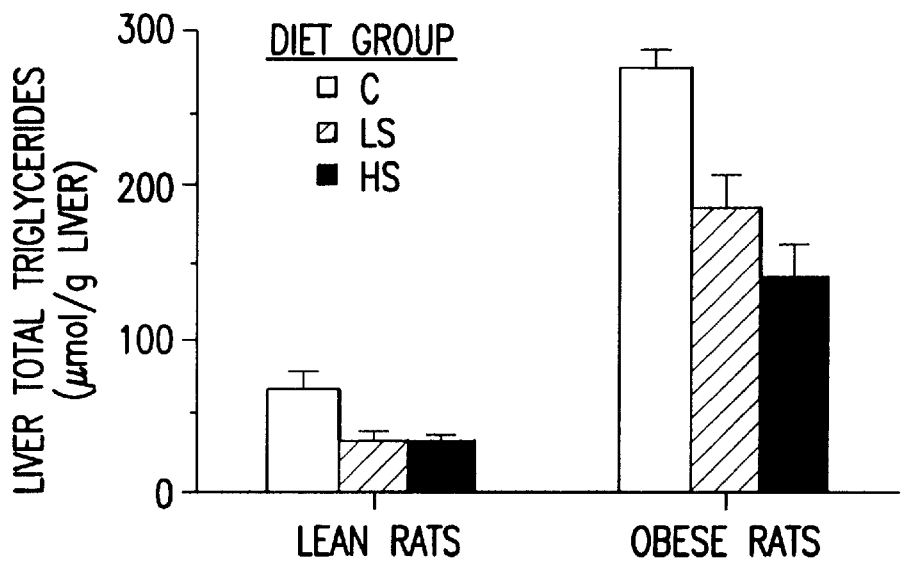
Figure 1D:
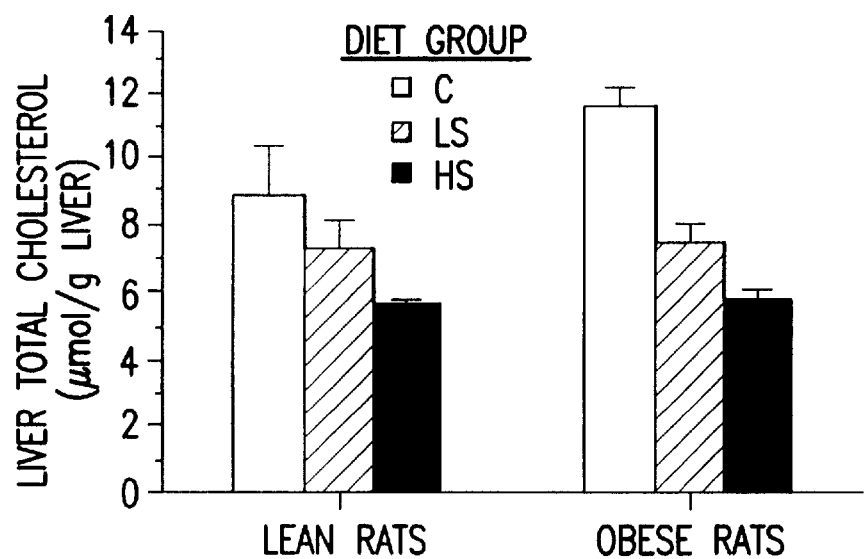
Figure 1E:
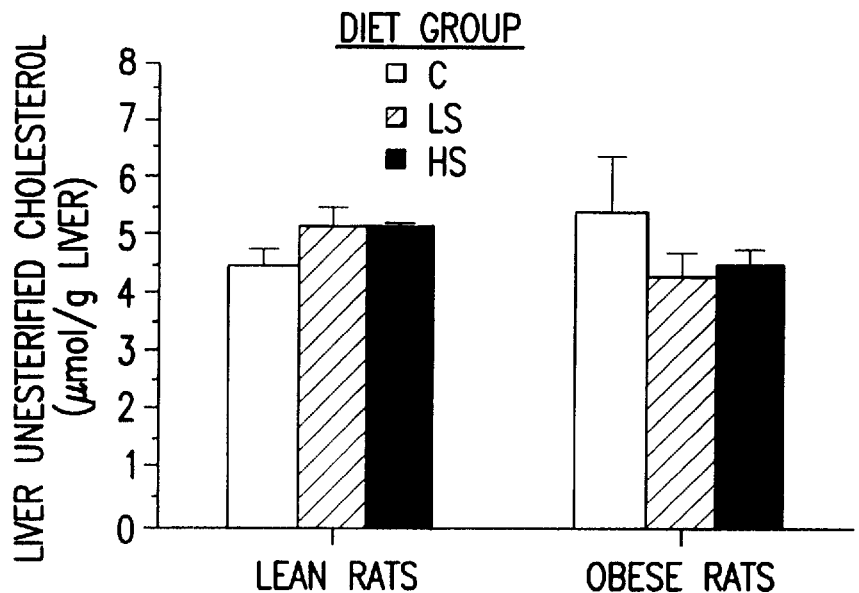
Figure 1F:
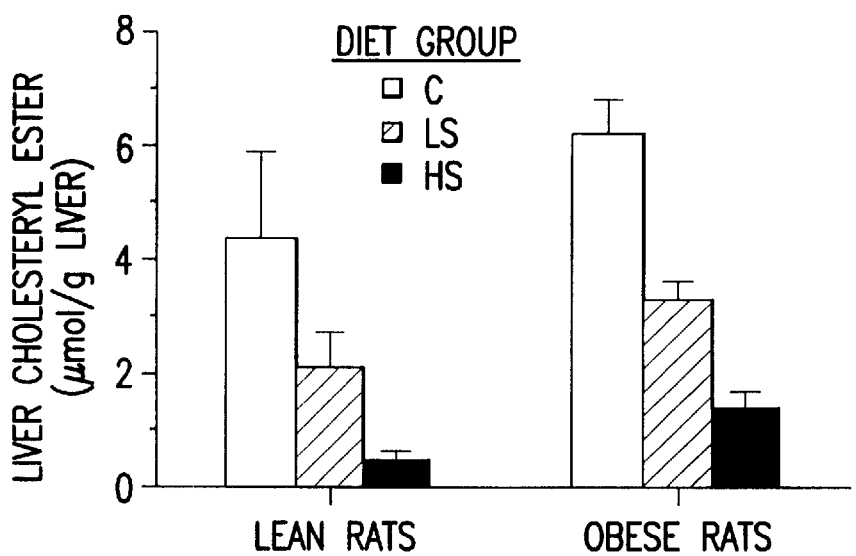

In the following description, reference will be made to various terms and methodologies known to those of skill in the biochemical and pharmacological arts. Publications and other materials setting forth such known terms and methodologies are incorporated herein by reference in their entireties as though set forth in full.

The present invention relates to a method of preventing or treating the symptoms of one or more of the following clinical medical conditions: hepatic steatosis, steatohepatitis, insulin resistance, impaired glucose tolerance, syndrome X, abnormal platelet function, or abnormal vascular reactivity. This method comprises administering to a subject having, or predisposed to, one or more of these conditions, a therapeutically effective amount of at least one isoflavonoid.

In a preferred embodiment the present invention provides a method for preventing or treating the symptoms of one or more of the aforementioned clinical medical conditions by administering to a subject having, or predisposed to, one or more of these conditions, a therapeutically effective amount of at least one isoflavonoid in combination with soy protein.

In another embodiment the present invention provides a method of preventing or treating the symptoms of one or more of the aforementioned clinical medical conditions by administering to a subject having, or predisposed to, one or more of these conditions, a therapeutically effective amount of at least one isoflavonoid in combination with dietary ingredients or supplements other than soy protein.

In another embodiment the present invention provides a method of preventing or treating the symptoms of one or more of the aforementioned clinical medical conditions by administering to a subject having, or predisposed to, one or more of these conditions, a therapeutically effective amount of at least one isoflavonoid which is contained in an isoflavone-enriched fraction of soy protein.

In another preferred embodiment the present invention provides a method of preventing or treating the symptoms of one or more of the aforementioned clinical medical conditions by administering to a subject having, or predisposed to, one or more of these conditions, a therapeutically effective amount of at least one isoflavonoid which is contained in an isoflavone-enriched fraction of soy protein in combination with soy protein.

In another embodiment the present invention provides a method of preventing or treating the symptoms of one or more of the aforementioned clinical medical conditions by administering to a subject having, or predisposed to, one or more of these conditions, a therapeutically effective amount of at least one isoflavonoid which is contained in an isoflavone-enriched fraction of soy protein in combination with dietary ingredients or supplements other than soy protein.

The following definitions and descriptions are provided to clarify the subject matter which the inventors consider to be the present invention.

As used herein, the term "hepatic steatosis" refers to lipid accumulation in hepatocyte cytoplasm.

As used herein, the term "steatohepatitis" refers to an inflammatory condition of the liver in which the hepatocytes demonstrate steatosis.

As used herein, the term "insulin resistance" refers to a condition in which the pancreas produces sufficient amounts of the hormone, but cells become desensitized to insulin's action and absorb it more slowly than normal, causing sugar (glucose) and insulin to accumulate in the blood.

As used herein, the term "Syndrome X" refers to a medical clinical condition which is characterized centralized obesity, high blood pressure, insulin resistance, increased LDL-cholesterol, decreased HDL-cholesterol, and elevated plasma insulin.

Isoflavones are a unique class of plant flavonoids that have a limited distribution in the plant kingdom and can be physically described as colorless, crystalline ketones. The most common isoflavone compounds are the conjugate, glucoside, and aglucone forms. The most common and important dietary source of these isoflavones are soybeans. In the present invention, the isoflavones are preferably selected from the following group: genistein, genistin, 6"-0-malonylgenistin, 6"-0-acetylgenistin; daidzein, daidzin, 6"-0-malonyldaidzin, 6"-0-acetylgenistin; glycitein, glycitin, 6"-0-malonylglycitin, 6"-0-acetylglycitin. Ninety-seven to ninety-eight percent of the soybean isoflavones are in the glycosylated form.

As used herein, the term "soy protein" refers either to "soy protein isolate" or "soy protein concentrate".

As used herein, the term "soy protein isolate " is equivalent to "isolated soy protein" and the same as "high-isoflavone soy protein" or "isoflavone-rich soy protein". This is soy protein that is isolated from soybeans by procedures that favor the adsorption of isoflavones (and other soybean constituents such as saponins) to the globular soybean proteins during the isolation process. This is one of the two types of soybean protein preparations used herein and referred to as a component of the "HS diet" or "HI diet", which is defined as the "high-isoflavone soy protein diet".

As used herein, the term "soy protein concentrate" refers to soy protein that is isolated from soybeans without accompanying isoflavones. "Soy protein concentrate" tends to be lower in total protein concentration than soy protein isolate.

As used herein, the term "low-isoflavone soy protein" is equivalent to "alcohol-washed soy protein" or "isoflavone depleted soy protein. The starting material is soy protein isolate. The soy protein isolate is then washed typically with an aqueous-ethanol mixture to remove adsorbed material, which includes isoflavones, saponins, and possibly other unidentified components of biological significance. This is the second of the two types of soy protein preparations used herein and referred to as a component of the "LS diet" or "LI diet", which is defined as the "low isoflavone soy protein diet".

As used herein, the term "isoflavone-enriched fraction of soy protein" consists of material that is removed from soy protein by washing the protein as described above. The isoflavones in the aqueous-ethanol extract are further purified to obtain a higher isoflavone concentration. This product can contain saponins and other biologically active material.

In one embodiment, the overall therapeutic benefit of high-isoflavone soy protein to reduce hepatic steatosis, insulin resistance, and platelet sensitivity is dependent on the protein component or another dietary ingredient(s) or supplement(s) other than soy protein that "mimics" the physiological action of soy protein in the intestinal tract to modulate cholesterol and bile acid absorption.

Various naturally-occurring and synthetic dietary ingredients and compounds have been shown to modulate intestinal lipid digestion and absorption. For example, the intestinal bile acid-binding resin, cholestyramine, potentiates the effects of soy isoflavones in the liver to produce therapeutic benefits. Methyl-$\beta$-cyclodextrin or hydroxypropyl-$\beta$-cyclodextrin which can form inclusion complexes with cholesterol and bile acids in the intestine, can be used in combination with isoflavones. Another possible embodiment is to use a dietary fiber source rich in silica polymers such as soy, rice, or oat hulls to modulate intestinal steroid homeostasis. Cooperativity between the liver and the intestinal tract is also achieved through combination of soy isoflavones or the isoflavone-enriched fraction of soy protein with classical sources of soluble dietary fiber (including pectin, $\beta$-glucan, oat bran, rice bran, psyllium fiber, and any other unspecified soluble cereal, vegetable, or fruit fiber preparations).

In another embodiment, fermentable soluble dietary fiber affects isoflavone bioavailability. Most isoflavones are present in soybeans as glycosylated isoflavone conjugates, and specific fiber types select for intestinal bacteria that produce enzymes required to produce the biologically-active aglycone forms.

The use of isoflavones, either singly or in combination with other soy proteins, dietary ingredients, or supplements to treat or prevent hepatic steatosis, steatohepatitis, insulin resistance, impaired glucose tolerance, syndrome X, abnormal platelet function, or abnormal vascular reactivity provides distinct advantages over currently administered pharmaceutical therapies. First, the present invention is likely to minimize the drug-related side effects that typically lead to non-compliance or untimely termination of treatment. Second, the use of naturally-occurring isoflavones overcomes some of the long term health concerns associated with current therapies which, in turn, increases the likelihood that individuals will remain on extended therapeutic regimens for sustained prevention of recurrent disease.

The term "therapeutically effective dosage" as used in the present invention is defined as the dosage which provides effective treatment or prevention of the above described conditions and/or diseases in both humans and animals.

In the treatment and prevention of hepatic steatosis, steatohepatitis, insulin resistance, impaired glucose tolerance, syndrome X, abnormal platelet function, or abnormal vascular reactivity, isoflavones, are administered in therapeutically effective dosages to subjects (humans or animals) diagnosed with one or more of the aforementioned clinical medical conditions or experiencing symptoms typically associated with them. The preventive aspect of the present invention involves administering therapeutically effective dosages of isoflavones to subjects at risk of developing one or more of the aforementioned clinical medical conditions. Other groups of subjects that are susceptible to the risk of developing will be apparent to those skilled in the art.

The metabolic products of the isoflavones contemplated for use in the present invention include equol and conjugates of genistein, daidzein, and other isoflavones. It is further contemplated that any derivative of other phytoestrogens including coumestans and lignans or conjugates thereof can be used in treating or preventing the conditions and/or diseases described hereinabove.

The isoflavone compounds can be naturally occurring substances which can be found in plants such as legumes, clover, and the root of the kudzu vine (pueraria root). Common legume sources of these isoflavone compounds include soy beans, chick peas, and various other types of beans and peas. Clover sources of these isoflavone compounds include red clover and subterranean clover. Soy beans are a particularly preferred source of the isoflavone compounds (except biochanin A which is not present in soy).

Isoflavones can be isolated from the plant sources in which they naturally occur, and several isoflavones can be synthetically prepared by processes known in the art. For example, daidzein can be isolated from red clover as disclosed by Wong *J Sci. Food Agr.* 13:304 (1962)) or can be isolated from the mold Micromonospora halophytica as provided by Ganguly and Sarre (Chem. & Ind (London), p. 201 (1970)), both references of which are incorporated by reference herein. Daidzein can be synthetically prepared by the methods provided by Baker et al.,(*J. Chem. Soc.* p. 274 (1933)), Wesley et al., *Ber.* 66: 685 (1933)), Mahal et al., *J. Chem. Soc.*, p. 1769 (1934)), Baker et al., *J. Chem. Soc.* p. 1852 (1953)), or Farkas *Ber.* 90:2940 (1957)), each reference of which is incorporated herein by reference. Daidzin can be synthetically prepared by the method of Farkas et al. *Ber.*, 92: 819 (1959)), incorporated herein by reference. The daidzein isoflavone conjugates 6'-OMal daidzin and 6'-OAc daidzin can be prepared by a conventional esterification of daidzin with a malonyl or an acetyl anhydride, respectively.

Genistein can be synthetically prepared by the methods provided by Baker et al (*J. Chem. Soc.*, p.3115 (1928)); Narasimhachari et al. (J. Sci. Ind. Res., Vol. 12, p. 287 (1953)); Yoder et al., (Proc. Iowa Acad. Sci., Vol. 61, p. 271 (1954); and Zemplen et al. (Acta. Chim. Acad. Sci. Hung., Vol. 19, p. 277 (1959)), each reference of which is incorporated herein by reference. Genistin can be synthetically prepared by the method of Zemplen et al. (Ber., Vol 76B, p. 1110 (1943)), incorporated herein by reference. The isoflavone conjugates of genistin, 6'-OMal genistin and 6'-OAc genistin, can be prepared by a conventional esterification of genistin with a malonyl or an acetyl anhydride, respectively.

Biochanin A can be synthetically prepared by the method provided by Baker et al. (Nature 169:706 (1952)), incorporated herein by reference. Biochanin A can also be separated from red clover by the method provided by Pope et al. (Chem. & Ind. (London) p. 1092 (1953)), incorporated herein by reference. Fornononetin can be synthetically prepared by the methods disclosed by Wessely et al. (Ber. 66:685 (1933)) and Kagel et al. (Tetrahedron Letters, p. 593 (1962)), both references of which are incorporated herein by reference. Fornononetin can be isolated from soybean meal by the method of Walz (Ann. 489:118 (1931)) or can be isolated from clover species by the method of Bradbury et al. (J. Chem. Soc. p. 3447 (1951)), both references of which are incorporated herein by reference.

A preferred method of isolating isoflavones from plant materials in which they naturally occur is to extract the plant materials with an alcohol, preferably methanol or ethanol, or an aqueous solution, preferably an aqueous alkaline solution, to remove the isoflavones from the plant material. It is preferred to comminute the plant material before extracting the isoflavones to maximize recovery of the isoflavone compounds from the plant material. The isoflavones can be isolated from the extract by conventional separation procedures such as reverse phase high performance liquid chromatography ("HPLC").

In a preferred embodiment, the isoflavones: genistein, genistin, 6'-OMal genistin, 6'-OAc genistin, daidzein, daidzin, 6'-OMal daidzin, 6'-OAc daidzin, glycitein, glycitin, and 6'-OMal glycitin are isolated from a soy material, preferably a commercially available soy material. Soy materials from which the isoflavones can be isolated include: soy beans, dehulled soy beans, soy meal, soy flour, soy grits, soy flakes (full fat and defatted), soy cotyldeons, soy molasses, soy protein concentrate, soy whey, soy whey protein, and soy protein isolate. In one embodiment, the isoflavones are extracted from soy beans, dehulled soy beans, soy meal, soy flour, soy grits, soy flakes, soy protein concentrate, soy whey protein, or soy protein isolate, preferably soy meal, soy flour, soy grits, or soy flakes, with a low molecular weight organic extractant, preferably an alcohol, ethyl acetate, acetone, or ether, and most preferably aqueous ethyl alcohol or methyl alcohol. Most preferably the extractant has a pH of about the isoelectric point of soy protein (about pH 4 to pH 5) to minimize the amount of soy protein extracted by the extractant.

A soy protein material for use in accordance with the method of the present invention is a whole soybean seed, or soy protein derivatives that can be formed from whole soybeans. Soy protein derivatives of whole soybeans include fat-containing or defatted: soy protein isolates, soy protein concentrates, soy flours, and soy meals which are formed in accordance with conventional methods for forming such materials. Soy protein derivatives of whole soybeans also include peptide materials which are formed by hydrolyzing soy protein containing materials in accordance with conventional methods for hydrolyzing soy protein materials, such as enzymatic or acid hydrolysis.

In a preferred embodiment, the soy protein material used in the method of the invention is a soy protein isolate. To form the isoflavone containing soy protein isolate, a commercially available defatted soy flake material is extracted with an aqueous alkaline solution, typically a calcium hydroxide or a sodium hydroxide solution having a pH of about 6 to about 10, to form an extract containing isoflavones, protein, and other water soluble components of the soy flake material. The extract is separated from insoluble soy materials and then is treated with an acid to lower the pH of the extract to about the isoelectric point of the protein, preferably to a pH of about 4 to about 5, and most preferably to a pH of about 4.4 to about 4.6, thereby precipitating a protein curd which captures significant amounts of the isoflavones as a result of hydrogen bonding between the protein and the isoflavones. Preferably the conjugate and glucoside isoflavones are converted to aglucone isoflavones in the extract as described above to increase the amount of aglucone isoflavones captured in the protein curd. The protein curd is then separated from the extract, preferably by centrifugation, and dried to form the protein isolate.

In another preferred embodiment, the soy protein material used in the method of the invention is a soy protein concentrate. To form the isoflavone containing soy protein concentrate, a commercially available defatted soy flake material is washed with an alcohol, preferably an aqueous alcohol such as 80% ethanol or 80% methanol, or an aqueous solution having a pH equivalent to the isoelectric point of soy protein, about pH 4.4 to about 4.6. The wash is separated from the protein material, leaving the soy protein concentrate.

The extractant containing the isoflavones is separated from the insoluble soy materials to form an isoflavone enriched extract. If desired, an isoflavone enriched material can be recovered by concentrating the extract to remove the solvent thereby producing a solid isoflavone enriched material. In another embodiment additional extract is added to the alcohol-washed soy protein (soy protein concentrate) to increase the amount of isoflavones in the protein concentrate.

In another preferred embodiment the isoflavones are further purified from other soy materials soluble in the extract by contacting the extract with a material which adsorbs the isoflavones in the extract, and eluting the adsorbed isoflavones out of the adsorbent material with a solvent which causes the isoflavones to be differentially eluted from the adsorbent material.

In another preferred embodiment the present invention provides a method of preventing or treating the symptoms of one or more of the aforementioned clinical medical conditions by administering to a subject having, or predisposed to, one or more of these conditions, a therapeutically effective amount of at least one isoflavone-enriched fraction component selected from the group consisting of a saponin, a lecithin, a phenolic acid, a trypsin inhibitor, a phytosterol, a peptide, and an oligosaccharide.

Having now fully described the invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in the entirety.

The following examples are illustrative, but not limiting, of the method and compositions of the present invention. Other suitable modifications and adaptations of the variety of conditions and parameters normally encountered and obvious to those skilled in the art are within the spirit and scope of the invention.

EXAMPLE I

Experimental Effects of Isoflavone-poor and Isoflavone-rich Soy Protein on Hepatic Lipids and Blood Platelet Activation Sensitivity in Male Lean and Obese Zucker Rats Animals and Diets.

Male Zucker obese (fa/fa) rats and their lean (Fa/Fa or Fa/fa) littermates (8 wk old, n=3 or n=4 lean per diet group, and n=5 obese per diet group, from Harlan Sprague-Dawley, Inc., Indianapolis, Ind.) were fed diets containing either casein (C diet), low-isoflavone soy protein isolate (LS diet), or high-isoflavone soy protein isolate (HS diet) as the protein source for 70 d. The basal (C) diet (Table 1) is a modified AIN-76 semi-purified diet for laboratory rodents. Sucrose was decreased from 500 g/kg diet (AIN-76 diet) to 300 g/kg diet, and cornstarch was increased from 150 g/kg diet (AIN-76 diet) to 350 g/kg diet. The net protein content of all 3 diets was 174 g/kg diet, and protein source (casein, low-isoflavone soy protein isolate, or high-isoflavone soy protein isolate) was the only dietary variable. Total isoflavone concentrations of the LS and HS diets were 3.8 mg/100 g diet and 57.8 mg/100 g diet, respectively. The individual isoflavone concentrations as genistein-, daidzein-, and glycitein-containing compounds (aglycones+glycosides+glycoside esters) were 2.4, 1.2, and 0.2 mg/100 g diet (LS diet) and 37.0, 17.9, and 2.9 mg/100 g diet (HS diet), respectively.

At the end of the 70 d experimental period, rats were deprived of food for 12 h, and then anaesthetized with an intraperitoneal injection of sodium pentobarbitol (5 mg/100g body wt). Blood was drawn from anaesthetized rats for platelet isolation by cardiac puncture into syringes pre-loaded with 10% of the expected blood volume as 4% sodium citrate. Livers were excised and frozen at −80° C. for cholesterol and triglyceride analysis. Platelets were isolated from platelet-rich plasma, and platelet activation sensitivity was estimated in vitro in resting and thrombin-stimulated platelets using the amount of serotonin (5HT) secreted (% initial platelet 5HT) as the dependent variable.

Liver Cholesterol and Triglyceride Analysis.

Portions of frozen-thawed livers were extracted with chloroform: methanol (2:1) essentially by the method of Folch, J., et al., *J. Biol. Chem.* 226:497–509(1957). For cholesterol analysis, aliquots of lipid extracts (5–50 µL) were mixed with 50 µL of 15% Triton X-100 in acetone, and solvents were evaporated under vacuum. Total and unesterified cholesterol concentrations were determined calorimetrically by an enzymatic procedure (Allain, C. C., et al., *Clin. Chem.* 20:470–475 (1974)), and cholesteryl ester was calculated by difference. Liver triglycerides were quantified (with a triolein standard) by a procedure utilizing the Hantzch reaction (Fletcher, M. J., *Clin. Chim. Acta* 22:393–397 (1968)).

Plasma Cholesterol Analysis.

Total cholesterol was measured in platelet-rich plasma using an enzymatic procedure (Allain, C. C., et al., *Clin. Chem.* 20:470–475 (1974)).

TABLE 1

Diet Composition[1]

| Ingredient | Control (C) | Low-isoflavone soy protein (LS) | High-isoflavone soy protein (HS) |
|---|---|---|---|
| | g/kg diet | | |
| Casein[2] | 200 | | |
| Soy protein[3] | | 200 | 200 |
| Cornstarch | 350 | 350 | 350 |
| Sucrose | 300 | 300 | 300 |
| Corn oil | 50 | 50 | 50 |
| Cellulose | 50 | 50 | 50 |
| Vitamin mix[4] | 10 | 10 | 10 |
| Mineral mix[4] | 35 | 35 | 35 |
| Choline chloride | 2 | 2 | 2 |

TABLE 1-continued

Diet Composition[1]

| | | Diet groups | |
|---|---|---|---|
| Ingredient | Control (C) | Low-isoflavone soy protein (LS) | High-isoflavone soy protein (HS) |
| DL-Methionine | 3 | 3 | 3 |
| α-Tocopherol | 1.2 | 1.2 | 1.2 |

[1]Total energy content = 15.67 MJ/kg diet. Macronutrient distribution (% metabolize energy, based on energy contents of 16.7 kJ/g protein. 37.6 kJ/g fat, and 16.7 kJ/g available carbohydrate, Wisker and Feldheim 1990): protein (18.6%), carbohydrate (69.4%), fat (12.0%).
[2]Casein, purified high nitrogen, 87% protein (ICN Biomedicals, Costa Mesa, CA).
[3]Soy protein isolates (Protein Technologies International, St. Louis, MO). Low-isoflavone soy protein (LS diet, Product FXP-H-0088), 86.4% protein, 3.5% fat, 4.4% ash, total isoflavones (0.2 mg/g product). High-isoflavone soy protein (HS diet, Product FXP-H-0086), 87% protein, 4.8% fat, 4.2% ash; total isoflavones (2.89 mg/g product).
[4]Vitamin and mineral mixes, AIN-76 (ICN Biomedicals, Costa Mesa, CA)

Platelet Isolation and Measurement of Platelet Activation Sensitivity.

Anticoagulated blood (8–9 mL) was mixed with 1.5 mL pH 7.4 buffered saline glucose-citrate (BSG-C), and platelet-rich plasma (PRP) was obtained by centrifugation at 850×g for 5 min at 22° C. The PRP was centrifuged through a two-step CellSep Platelets (Cardinal Associates, Santa Fe, NM) gradient at 1450×g for 20 min at 22° C. Isolated platelets were removed from the gradient interface, washed with BSG-C, and re-suspended in pH 7.6 Tyrode's buffer at a concentration of 2–4×10$^8$ cells per mL. Aliquots of suspended platelets were equilibrated at 22° C. for 3 h, and then -treated either with or without thrombin (0.15 U/mL) for 3 min. Thrombin-stimulated and unstimulated platelets were pelleted, and supernatants were immediately removed and frozen at –80° C. Platelet pellets were dissolved in pH 7.5 lysis buffer, and protein was quantified essentially by the method of Lowry, O. H., et al., *J. Biol Chem*. 193:265–275 (1951) using Sigma Assay Kit no. P5656 and BSA as a standard. Aliquots of thrombin-stimulated and unstimulated platelet lysates and supernatants were diluted with 0.32 M perchloric acid containing methyl 5-hydroxytryptamine (methylserotonin) as an internal standard. Serotonin was quantified using reverse-phase HPLC. The initial platelet serotonin content was computed by adding the amount of serotonin in each platelet lysate to the amount of serotonin secreted from each suspended platelet sample. Serotonin secreted from unstimulated and thrombin-stimulated platelet samples is expressed as a percentage of the initial platelet serotonin content (% initial platelet 5HT).

Statistical Analysis.

Figure 2:
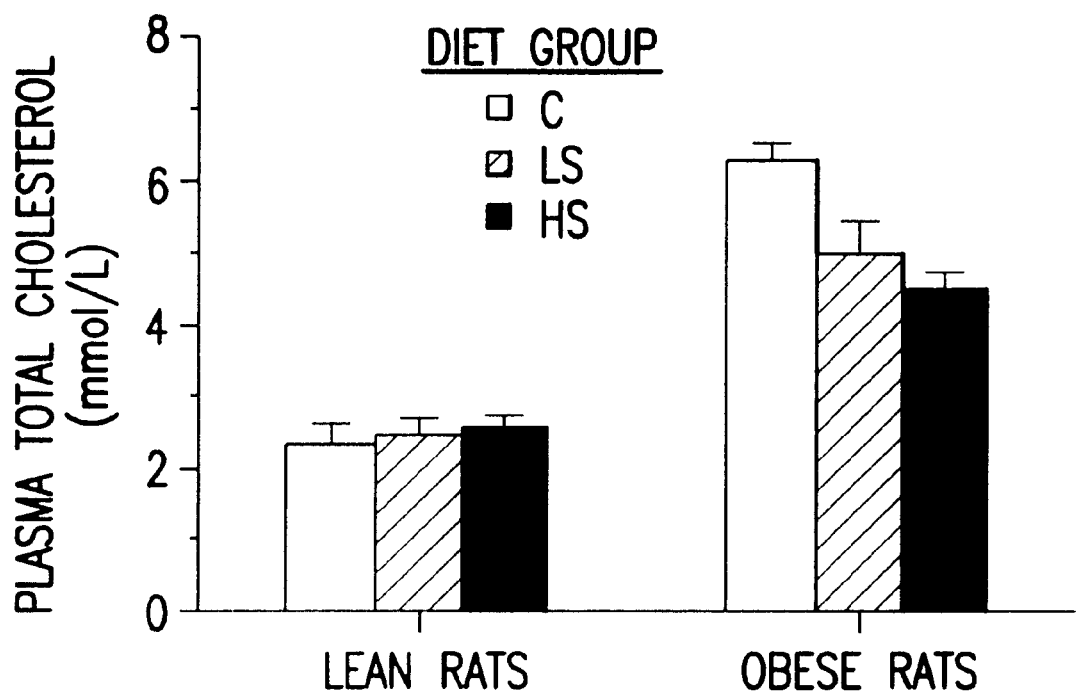
FIG. 2 shows a bar graph depicting the plasma total cholesterol concentration in male lean and obese Zucker rats fed casein, isoflavone-poor soy protein (LS), or isoflavone-rich (HS) soy protein-based diets for 70 days.
Figure 3A:
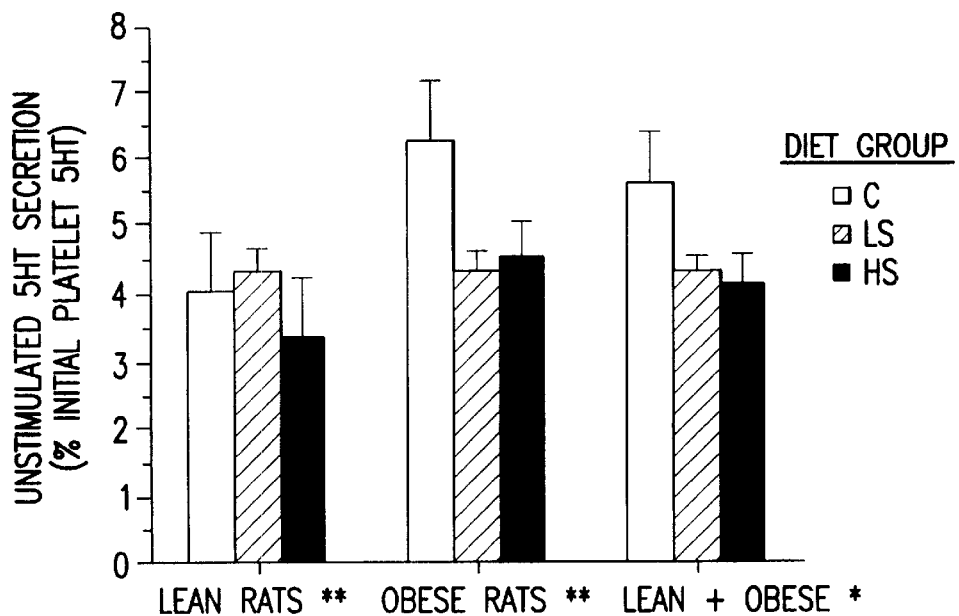
FIGS. 3A–B shows two bar graphs depicting serotonin (5HT) secretion from unstimulated and thrombin-stimulated platelets isolated from male lean and obese Zucker rats fed casein, isoflavone-poor soy protein (LS), or isoflavone-rich (HS) soy protein-based diets for 70 days.
Figure 3B:
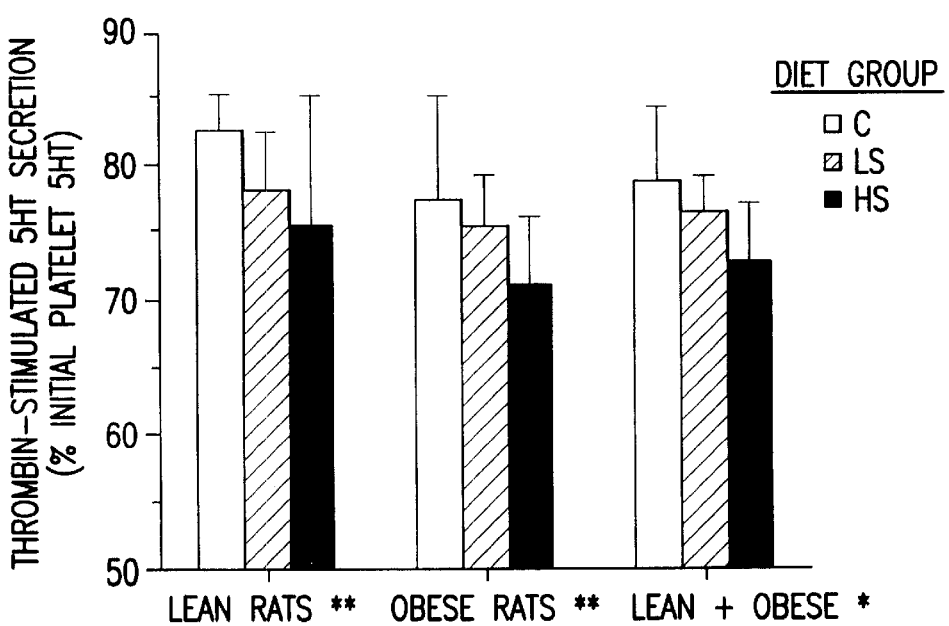

Body weights, weight gain, energy intake, and energy efficiency ratio were analyzed for the main and interaction effects of diet group (C, LS, and HS) and phenotype (lean, obese), using a two-way ANOVA. Liver cholesterol and triglyceride and plasma cholesterol concentrations were similarly analyzed, and results provided in FIGS. 1 and 2 are given as diet group means ±SEM. Platelet data was analyzed for the main and interaction effects of diet group (C, LS, and HS) and phenotype (lean, obese) using either two-way ANOVA (for platelet protein and initial platelet 5HT) or two-way ANCOVA with platelet protein as a covariate (for unstimulated 5HT secretion and thrombin-stimulated 5HT secretion). Results provided in FIG. 3 are given as diet group least-squares means ±SEM. Platelet data was also analyzed for the effects of diet group (C, LS, and HS), independent of phenotype, using either a one-way ANOVA or a one-way ANCOVA as described above.

Results.

Initial and final body weights averaged 183 g and 408 g, respectively in lean rats and 242 g and 584 g, respectively in obese rats. This corresponded to an average weight gain of 3.2 g/d in lean rats and 4.9 g/d in obese rats. Energy intake and energy efficiency ratio averaged 360 kJ/d and 9.0 g/MJ, respectively in lean rats and 441 kJ/d and 11.1 g/MJ, respectively in obese rats. The effect of phenotype was significant (P<0.001), but the effect of diet group was not significant (P>0.05) for each variable.

Liver weight (FIG. 1A) in obese rats was reduced by soy protein from 27.2 g (C diet) to 20.4 g (LS diet) to 15.5 g (HS diet). This corresponded to a reduction in relative liver weight (FIG. 1B) from 4.9 g/100 g body wt (C diet) to 3.6 g/ 100 g body wt (LS diet) to 2.7 g/100 g body wt (HS diet). Liver triglycerides (FIG. 1C) were lowered in lean rats by both soy protein diets from 67 μmol/g liver (C diet) to 34–36 μmol/g liver (LS and HS diets), as well as in obese rats from 279 μmol/g liver (C diet) to 187 μmol/g liver (LS diet) to 142 μmol/g liver (HS diet). Liver total cholesterol (FIG. 1D) was lowered from 8.9 μmol/g liver and 11.8 μmol/g liver in lean and obese rats (C diet), respectively, to 5.8–6.1 μmol/g liver (HS diet). Although a consistent effect of soy protein on liver unesterified cholesterol (FIG. 1E) was not observed, liver cholesteryl ester (FIG. 1F) was dramatically reduced from control values (C diet) by the HS diet, in both lean and obese rats, by 88% and 77%, respectively. The LS diet produced an intermediate lowering of liver cholesteryl ester and total cholesterol in lean and obese animals. Plasma total cholesterol (FIG. 2) was not affected by diet in lean rats; however, plasma cholesterol was decreased in obese rats from 6.3 mmol/L (C diet) to 5.0 mmol/L (LS diet) to 4.5 mmol/L (HS diet).

Platelet protein concentration averaged 165 μg/sample in lean and obese rats, independent of diet group or phenotype. Initial platelet 5HT (serotonin) concentration tended to be higher (P=0.07) in obese rats (2.5 ng/μg protein) than in lean rats (2.1 ng/μg protein), independent of diet group. There was not a significant effect of diet group or phenotype on either unstimulated 5HT secretion (FIG. 3A) or thrombin-stimulated 5HT secretion (FIG. 3B); although, unstimulated 5HT secretion tended to be higher (P=0.1) in obese rats (5.0%) than in lean rats (3.9%). Furthermore, there was a significant reduction (one-way ANCOVA, P=0.04) in unstimulated 5HT secretion from 5.6% (C diet) to 4.1% (HS diet), as well as a tr end for a reduction (P=0.06) to 4.3% bv the LS diet.

EXAMPLE II

Experimental Effects of Isoflavone-poor and Isoflavone-rich Soy Protein on Hepatic Lipids and Blood Platelet Activation Sensitivity in Male Sprague-Dawley Rats Animals, Diets, and Analytical Procedures.

Male Sprague-Dawley rats (6 wk old, n=10 per diet group, from Harlan Sprague-Dawley, Inc., Indianapolis, Ind.) were fed diets containing either casein (C diet), low-isoflavone soy protein isolate (LS diet), or high-isoflavone soy protein isolate (HS diet) as the protein source for 42 d. Diets were identical to those listed in Table 1 (Example I). Analytical procedures for determination of liver cholesterol and triglyceride concentrations, plasmna total cholesterol concentration, and platelet activation sensitivity were as described in Section I.

Statistical Analysis.

Figure 4A:
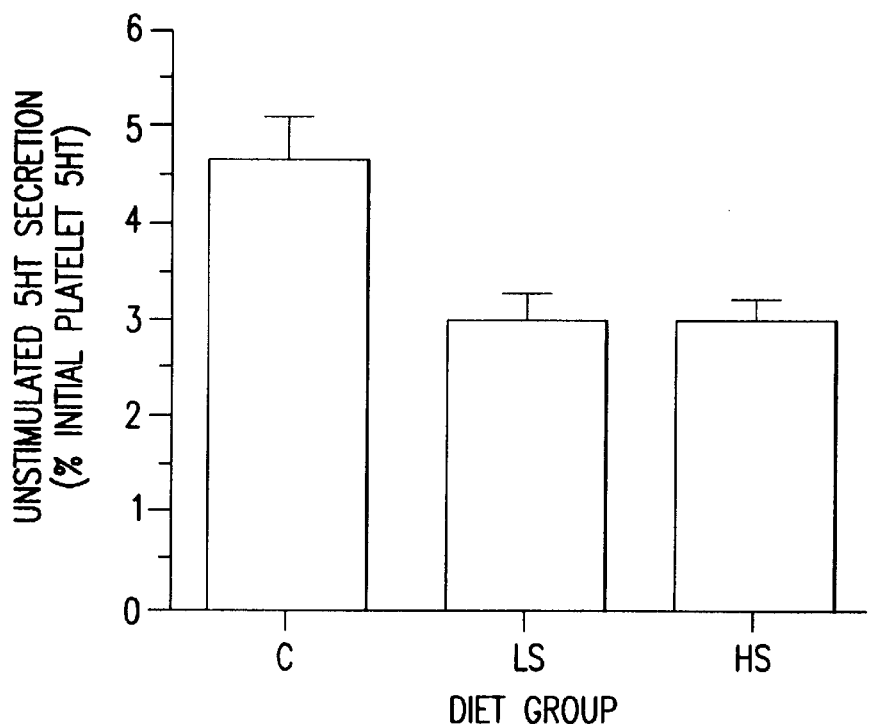
FIGS. 4A–B shows two bar graphs depicting serotonin (5HT) secretion from unstimulated and thrombin-stimulated platelets isolated from male Sprague-Dawley rats fed casein, isoflavone-poor soy protein (LS), or isoflavone-rich (HS) soy protein-based diets for 42 days.
Figure 4B:
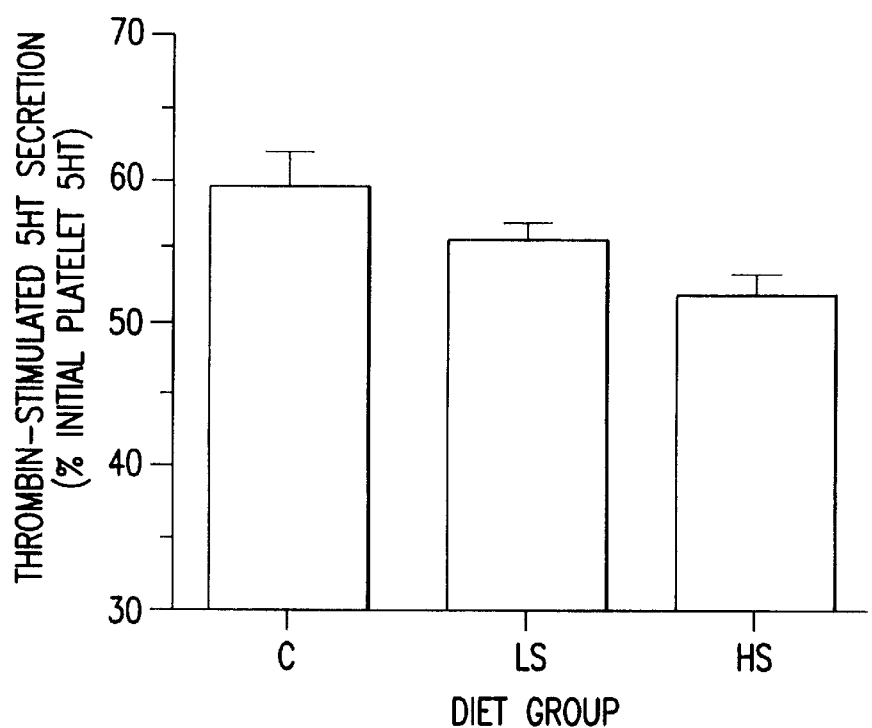

Body weights, weight gain, energy intake, and energy efficiency ratio were analyzed for the effect of diet group (C, LS, and HS), using a one-way ANOVA. Liver cholesterol and triglyceride concentrations and plasmatotal cholesterol concentration were analyzed similarly (Table 2). Platelet data was analyzed for the effect of diet group, using either one-way ANOVA (for platelet protein and initial platelet 5HT) or one-way ANCOVA with platelet protein as a covariate (for unstimulated 5HT secretion and thrombin-stimulated 5HT secretion). Results provided in FIG. 4 are given as diet group least-squares means±SEM.

TABLE 2

Plasma Cholesterol Concentration and Liver Cholesterol and Triglyceride Concentrations in Male Sprague-Dawley Rats Fed Casein-, Isoflavone-poor Soy Protein-, or Isoflavone-rich Soy Protein-based Diets for 42 Days[1]

| Diet group[2] | n | Plasma total cholesterol[3] mmol/L | Liver weight[4] g/100 g body wt | Unesterified cholesterol | Cholesteryl esters[5] | Total cholesterol | Total triglycerides[5,6] |
|---|---|---|---|---|---|---|---|
|  |  |  |  | μmol/g liver | | | |
| C | 10 | 2.70 | 2.99 | 4.50[b] | 2.60 | 7.10 | 22.94 |
| LS | 10 | 2.66 | 2.78 | 4.63[b] | 2.39 | 7.02 | 19.08 |
| HS | 10 | 2.54 | 2.82 | 4.98[a] | 1.99 | 6.97 | 16.82 |
| Pooled SEM |  | 0.05 | 0.04 | 0.07 | 0.13 | 0.12 | 1.36 |

[1]Values are diet group means. Values in a column not sharing a common superscript are significantly different (one-way ANOVA, Fisher's LSD test, $P \leq 0.05$).
[2]Diet groups: C, control; LS, low-isoflavone soy protein; HS, high-isoflavone soy protein
[3]Values are for platelet-rich plasma.
[4]Liver weight (g/100 g body wt) tended to be lower in the LS and HS groups than in the C group ($P \leq 0.1$).
[5]Liver cholesteryl ester and triglyceride concentrations tended to be lower in the HS group than in the C group ($P \leq 0.1$).
[6]Total triglycerides as triolein (MW 885.4).

Results.

Initial and final body weights averaged 125 g and 341 g, respectively, independent of diet group. This corresponded to a weight gain of 5.1 g/d. Energy intake was lower in rats fed the LS diet (310 kJ/d) and the HS diet (324 kJ/d) than in rats fed the C diet (352 kJ/d), and the energy efficiency ratio increased from 14.5 g/MJ (C diet) to 16.6 g/MJ (LS diet) and 16.0 g/MJ (HS diet).

Relative liver weight (Table 2) tended to be lower ($P \leq 0.1$) in the LS and HS diet groups (2.8 g/100 g body wt) than in the C diet group (3.0 g/100 g body wt). There was a trend towards a 23% reduction in liver cholesteryl ester and a 27% reduction in liver total triglycerides from control (C diet) values by the HS diet ($P \leq 0.1$). Liver unesterified cholesterol was increased ($P \leq 0.05$) from 4.5 μmol/g liver (C diet) and 4.6 μmol/g liver (LS diet) to 5.0 μmol/g liver in rats fed isoflavone-rich soy protein (HS diet). Plasma total cholesterol concentration was not significantly affected by diet group.

Platelet protein concentration and the initial platelet 5HT (serotonin) concentration averaged 211 μg/sample and 3.1 ng/μg protein, respectively, independent of diet group. Unstimulated 5HT secretion (FIG. 4A) was lowered by both soy protein diets from 4.7% (C diet) to 3.0%. Thrombin-stimulated 5HT secretion (FIG. 4B) was reduced from 59.7% (C diet) to 52.2% (HS diet); whereas, the LS diet tended to produce an intermediate reduction (P=0.1) to 55.9%.

EXAMPLE III

Experimental Effects of Soy Isoflavones on Hepatic Lipids and Blood Platelet Activation Sensitivity in Male Sprague-Dawley Rats Fed Control or Athlerogenic Diets Animals, Diets, and Analytical Procedures.

Male Sprague-Dawley rats (8 wk old, n=10 per diet group, from Harlan Sprague-Dawley, Inc., Indianapolis, Ind.) were fed either a control (C) diet (n=20) or an atherogenic (A) diet (n=30) for 63 d. Diet compositions are given in Table 3. One-half of the rats administered the control diet (C+I diet) and one-third of the rats administered the atherogenic diet (A+I diet) were fed the control or atherogenic diet supplemented with a soy isoflavones extract that provided 98.3 mg total isoflavones per 100 g diet. Additionally, one-third of the rats administered the atherogenic diet (A+HS diet) were fed the atherogenic diet with casein replaced by high-isoflavone soy protein isolate (57.8 mg total isoflavones per 100 g diet). The individual isoflavone concentrations as genistein-, daidzein-, and glycitein-containing compounds (aglycones+glycosides+glycoside esters) were 53.5,41.1, and 3.7 mg/100 g diet (C+I and A+I diets) and 37.0, 17.9, and 2.9 mg/100 g diet (A+HS diet). The basal diet (C diet) is a modified AIN-76 semipurified diet for laboratory rodents. For the basal diet, sucrose was decreased from 500 g/kg diet (AfN-76 diet) to 200 g/kg diet, and cornstarch was increased from 150 g/kg diet (AIN-76 diet) to 450 g/kg diet. The net protein content of all five diets was 174 g/kg diet. The control diet was converted to an atherogenic diet by increasing the sucrose content from 200 to 400 g/kg diet, reducing the cornstarch content from 450 to 145 g/kg diet, reducing the corn oil content from 50 to 20 g/kg diet, and by adding coconut oil (70 g/kg diet), lard (50 g/kg diet), cholesterol (12 g/kg diet), and cholic acid (2 g/kg diet). Analytical procedures for determination of liver cholesterol and triglyceride concentrations, plasma total cholesterol concentration, and platelet activation sensitivity were as described in Example I.

Statistical Analysis.

Figure 5A:
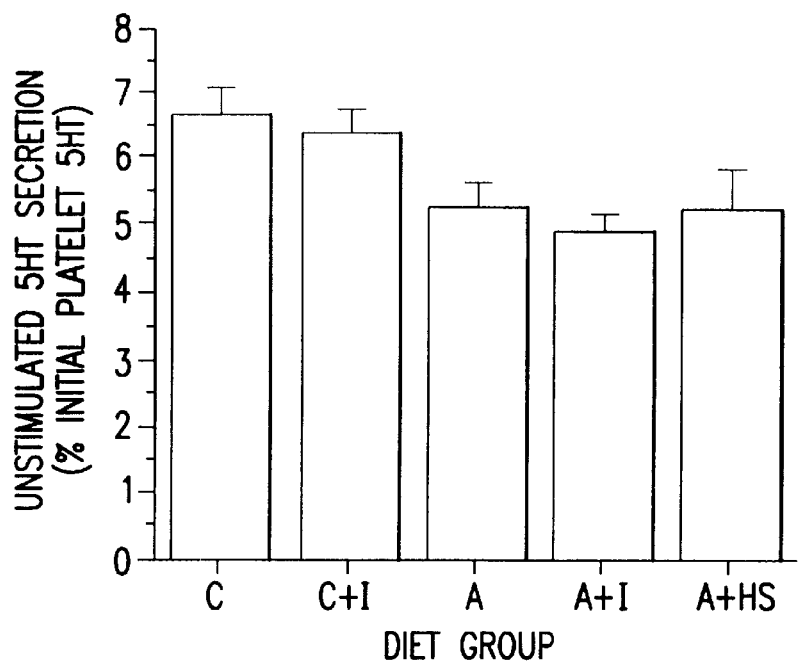
FIGS. 5A–B shows two bar graphs depicting serotonin (5HT) secretion from unstimulated and thrombin-stimulated platelets isolated from male Sprague-Dawley rats fed control or atherogenic diets with or without soy isoflavones for 63 days.
Figure 5B:
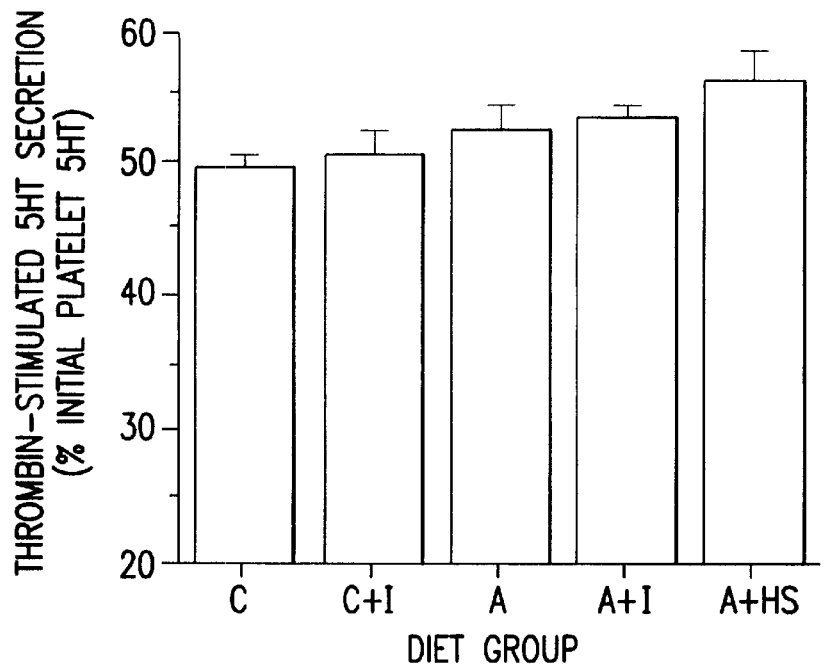

Body weights, weight gain, energy intake, and energy efficiency ratio were analyzed with a two-way ANOVA for the main and interaction effects of type of diet (C and C+I diets vs. A, A+I, and A+HS diets) and the presence of isoflavones in the diet (C and A diets vs. C+I, A+I, and A+HS diets). Liver cholesterol and triglyceride and plasma cholesterol concentrations (Table 4) were similarly analyzed. Additionally, a one-way ANOVA was applied to the liver lipid and plasma cholesterol data to distinguish individual treatment effects among the three atherogenic diets. Platelet data was analyzed for the main and interaction effects of type of diet and the presence of isoflavones in the diet as described above, using either two-way ANOVA (for platelet protein and initial platelet 5HT) or two-way ANCOVA with platelet protein as a covariate (for unstimulated 5HT secretion and thrombin-stimulated 5HT secretion). Results provided in FIG. 5 are given as individual diet group least-squares means±EM.

TABLE 3

Diet Composition[1]

| Ingredient | Diet Groups | | | | |
|---|---|---|---|---|---|
| | Control (C) | Control + soy isoflavones (C + I) | Atherogenic (A) | Atherogenic + soy isoflavones (A + I) | Atherogenic + soy protein (A + HS) |
| | g/kg diet | | | | |
| Casein[2] | 200 | 200 | 200 | 200 | |
| Soy Protein[3] | | | | | 200 |
| Cornstarch | 450 | 450 | 145 | 145 | 145 |
| Sucrose | 200 | 200 | 400 | 400 | 400 |
| Corn oil | 50 | 50 | 20 | 20 | 20 |
| Coconut oil | | | 70 | 70 | 70 |
| Lard | | | 50 | 50 | 50 |
| Cellulose | 50 | 50 | 50 | 50 | 50 |
| Vitamin mix[4] | 10 | 10 | 10 | 10 | 10 |
| Mineral mix[4] | 35 | 35 | 35 | 35 | 35 |
| Choline Chloride | 2 | 2 | 2 | 2 | 2 |
| DL-Methionine | 3 | 3 | 3 | 3 | 3 |
| α-Tocopherol | 1.2 | 1.2 | 1.2 | 1.2 | 1.2 |
| Cholesterol | | | 12 | 12 | 12 |
| Cholic acid | | | 2 | 2 | 2 |
| Soy isoflavones[5] | | 1.2 | | 1.2 | |

[1]Total energy content = 15.67 MJ/kg diet (C and C + I diets) and 17.31 MJ/kg diet (A, A + I, and A + HS diets). Macronutrient distribution (% metabolize energy, based on energy contents of 16.7 kJ/g protein, 37.6 kJ/g fat, and 16.7 kJ/g available carbohydrate, Wisker and Feldheim 1990): C and C + I diets, protein (18.6%), carbohydrate (69.4%), fat (12.0%); A, A + I, and A + HS diets, protein (16.8%), carbohydrate (52.7%), fat (30.5%).
[2]Casein, purified high nitrogen, 87% protein (ICN Biomedicals, Costa Mesa, CA).
[3]Soy protein isolate (Protein Technologies International, St. Louis, MO). High-isoflavone soy protein (HS diet, Product FXP-H-0086), 87% protein, 4.8% fat, 4.2% ash; total isoflavones (2.89 mg/g product).
[4]Vitamin and mineral mixes, AIN-76 (ICN Biomedicals, Costa Mesa, CA).
[5]Soy Isoflavones (Archer Daniels Midland, Decatur, IL). Total isoflavones (833 mg/g product).

Results.

Initial and final body weights averaged 183 g and 420 g, respectively, independent of the type of diet or the presence of isoflavones. This corresponded to an average weight gain of 3.8 g/d. Despite similar growth rates for each of the five treatment groups, energy intake was lowered ($P \leq 0.001$) from an average of 355 kJ/d in rats fed control diets (C and C+I diets) to 302 kJ/d in rats fed atherogenic diets (A, A+I, and A+HS diets). Furthermore, energy intake was increased ($P \leq 0.002$) from an average of 315 kJ/d in rats fed diets not containing isoflavones (C and A diets) to 329 kJ/d in rats fed diets containing isoflavones (C+I, A+I, and A+HS diets).

Correspondingly, the energy efficiency ratio was increased ($P \leq 0.001$) from an average of 10.4 g/MJ in rats fed control diets to 12.7 g/MJ in rats fed atherogenic diets, and decreased ($P \leq 0.001$) from an average of 12.3 g[MJ in rats fed diets without isoflavones to 11.5 g/MJ in rats fed diets with isoflavones.

Liver weight (Table 4) was increased ($P \leq 0.001$) from an average of 2.6 g/100 g body wt in rats fed control diets (C and C+I diets) to 4.4 g/100 g body wt in rats fed atherogenic diets (A, A+I, and A+HS diets). Among the atherogenic diet groups, liver weight was significantly higher ($P \leq 0.01$) in rats fed the A+I diet (4.7 g/100 g body wt) than in rats fed the A and A+HS diets (4.3 and 4.2 g/100 g body wt, respectively). Liver unesterified cholesterol was increased from an average of 4.4 μmol/g liver and liver cholesteryl ester was increased from an average of 1.7 μmol/g liver in rats fed control diets to 9.3 μmol/g liver and 104.8 μmol/g liver, respectively, in rats fed atherogenic diets ($P \leq 0.001$). Liver total triglycerides were also increased from an average of 16.0 μmol/g liver to 46.8 μmol/g liver by the atherogenic diet ($P \leq 0.001$). Among the atherogenic diet groups, liver unesterified cholesterol was significantly higher ($P < 0.01$) and liver triglycerides were significantly lower ($P \leq 0.001$) in rats fed atherogenic diets with isoflavones (A+I and A+HS diets) than in rats fed the atherogenic diet without isoflavones (A diet). Plasma total cholesterol concentration was increased ($P \leq 0.001$) from an average of 2.6 mmol/L in rats fed control diets to 4.7 mmol/L in rats fed atherogenic diets and was higher ($P \leq 0.05$) in rats fed the A+I diet (5.1 mmol/L) than in rats fed the A+HS diet (4.4 mmol/L).

TABLE 4

Plasma Cholesterol Concentration and Liver Cholesterol and Triglyceride Concentrations in Male Sprague-Dawley Rats Fed Control or Atherogenic Diets with or without Soy Isoflavones for 63 Days[1]

| Diet Group[2] | n | Plasma total cholesterol[3] mmol/L | Liver Wt. g/100 g body wt | Unesterified cholesterol | Cholesteryl esters | Total cholesterol | Total triglycerides[4] |
|---|---|---|---|---|---|---|---|
| | | | | μmol/g liver | | | |
| C | 10 | 2.56 | 2.57 | 4.33 | 1.55 | 5.88 | 15.73 |
| C + I | 10 | 2.62 | 2.62 | 4.46 | 1.95 | 6.40 | 17.19 |
| A | 10 | 4.64 | 4.28 | 8.42 | 97.90 | 106.31 | 59.62 |
| A + I | 10 | 5.08[c] | 4.70[d] | 9.87[e] | 106.83 | 116.69 | 40.10[f] |
| A + HS | 10 | 4.43 | 4.18 | 9.63[e] | 109.74 | 119.37 | 40.62[f] |
| Pooled SEM | | 0.18 | 0.14 | 0.37 | 7.69 | 8.04 | 2.77 |
| Effects | | | | Two-way ANOVA | | | |

TABLE 4-continued

Plasma Cholesterol Concentration and Liver Cholesterol and Triglyceride Concentrations in Male Sprague-Dawley Rats Fed Control or Atherogenic Diets with or without Soy Isoflavones for 63 Days[1]

| | P-value[5] | | | | | |
|---|---|---|---|---|---|---|
| Diet | 0.001 | 0.001 | 0.001 | 0.001 | 0.001 | 0.001 |
| Soy Isoflavones | NS | NS | 0.01 | NS | NS | 0.01 |
| Diet x soy isoflavones | NS | NS | 0.04 | NS | NS | 0.001 |

[1]Values are diet group means.
[2]Diet groups: C, control; C + I, control + soy isoflavones; A, atherogenic; A + I, atherogenic + soy isoflavones; A + HS, atherogenic + high-Isoflavone soy protein.
[3]Values are for platelet-rich plasma
[4]Total triglycerides as triolein (MW 885.4).
[5]Actual P-values for two-way ANOVA are less than or equal to values shown.
[c]Significantly higher than the A + HS group (one-way ANOVA, Fisher's LSD test, $P \leq 0.05$).
[d]Significantly higher than the A and A + HS groups (one-way ANOVA, Fisher's LSD test, $P \leq 0.01$).
[e]Significantly higher than the A group (one-way ANOVA, Fisher's LSD test, $P \leq 0.01$).
[f]Significantly lower than the A group (one-way ANOVA, Fisher's LSD test, $P \leq 0.001$).

Platelet protein concentration averaged 312 µg/sample and was not affected by type of diet or dietary isoflavones. However, the initial platelet 5HT concentration was lowered (P<0.001) from an average of 2.4 ng/µg protein in rats fed control diets (C and C+I diets) to 1.9 ng/µg protein in rats fed atherogenic diets (A, A+1. and A+HS diets). Unstimulated 5HT secretion (FIG. 5A) was decreased ($P \leq 0.001$) from an average of 6.5% to 5.2%, and thrombin-stimulated 5HT secretion (FIG. 5B) was increased ($P \leq 0.02$) from an average of 50.1% to 54.4% in rats fed atherogenic diets. The presence of dietary isoflavones either as an isoflavone extract (C+I and A+I diets) or as a component of soy protein (A+HS diet) did not significantly affect unstimulated or thrombin-stimulated 5HT secretion.

EXAMPLE IV

The Effect of Genistein, Daidzein and Estradiol on Liver and Metabolic Parameters in Male Sprague-Dawley Rats Animals and Treatments.

Forty male Sprague-Dawley rats (5 wk old, n=9–10 rats/treatment, from Harlan Sprague-Dawley, Inc., Indianapolis, Ind.) were injected with either genistein (G), daidzein (D), estradiol (E), or a vehicle control (V). Each animal in group V received a daily 0.1 cc subcutaneous injection, for six weeks, of a 10% ethanol-90% olive oil solution; the other treatments received their respective compound as a daily 0.1 cc subcutaneous injection, for six weeks, e.g., 0.1 µg of compound/g of body weight, in a 10% ethanol-90% olive oil solution.

Feed and Weight Measurements.

Animal weight and feed intake were measured weekly during the six week study, and the subsequent feed-efficiency ratio [FER (g of weight change/g of feed intake)] was determined. Following sacrifice, the abdominal fat pads, liver, and reproductive organs were removed and weighed for comparison.

Plasma Glucose and Plasma Total Cholesterol Analysis.

Collected blood was heparinized and centrifuged, plasma aliquots were then used for glucose and total cholesterol determinations, using standard glucose oxidase (Fisher Scientific, St. Louis, Mo.) and cholesterol kits (Fisher Scientific, St. Louis, Mo.). Liver cholesterol and triglyceride analysis. Analytical procedures for determination of liver total cholesterol, unesterified cholesterol, cholesteryl ester, and triglyceride concentrations were as described in Example 1.

Liver Cu, Zn Superoxide Dimutase and Catalase Analysis.

The activity or level of antioxidant enzymes (AOE), catalase (CAT) and Cu,Zn superoxide Dimutase (SOD) in rat liver, were measured to determine the effect of administration of G, D, and E injections on free radical defense systems. A 50 mg piece of whole frozen liver was removed and sonicated in TBS plus 1% Triton X-100. The samples were then centrifuged at 13,000×g for 25 min at 4° C., and the supernatant was collected. Total protein concentration was assayed for subsequent determinations of hepatic AOE activity or absolute level per milligram total protein. SOD activity was determined by spectrophotometry at I=560 nm using xanthine/xanthine oxidase as a superoxide generator and measured against a standard curve of known SOD activities (Sun et al. 1988, 1994). Catalase levels were determined by Slot blot, which was performed following a representative Western blot that detected no nonspecific binding (Tobin et al. 1979). The bands corresponding to catalase were quantified by densitometry.

Statistical Analysis.

These studies used a randomized design. All data were analyzed by one-way analysis of variance (ANOVA) and post-hoc comparisons were made with Tukey pairwise comparisons test. Significance was confirmed at $P \leq 0.05$ (SYSTAT 7.0, SPSS INC., 1997), and all values are reported as means±standard error of the mean.

Results.

Feed and Weight Measurements:

Feed intake was significantly (P<0.05) higher in the D, G and E treated animals when compared to V treated animals (Table 5). Body, testis, and prostate weight were markedly (P<0.05) lower in the E treated animals when compared to D, G, and V treated animals. Consequently, FER was lower (P<0.05) in D, G, and E treated animals when compared to V, and the E treated animals had notably (P<0.05) lower FER vs D and G treatments. Intraabdominal fat pad weights were significantly (P<0.05) lower in the E group; although, this effect was lost when corrected for body weight.

TABLE 5

Feed Intake, Body Weight, Visceral Fat Weight, Testis Weight and Prostate Weight in Male Sprague-Dawley Rats Injected with Control, Genistein, Daidzein, or Estradiol for 6 Weeks[1]

| Injection Group[2] | n | FER[3] | Feed Intake | Body Weight | Fat Weight | Testis Weight | Prostate Weight |
|---|---|---|---|---|---|---|---|
| | | | | | g | | |
| V | 10 | .327 | 721.30 | 364.60 | 11.86 | 3.19 | .672 |
| G | 9 | .277 | 855.80[a] | 363.00 | 11.19 | 2.90 | .732 |
| D | 10 | .284 | 857.44[a] | 367.89 | 11.66 | 2.96 | .671 |
| E | 10 | .137 | 852.10[a] | 242.50[a,b,c] | 6.71[a,b,c] | 1.44[a,b,c] | .291[a,b,c] |

Figure 6:
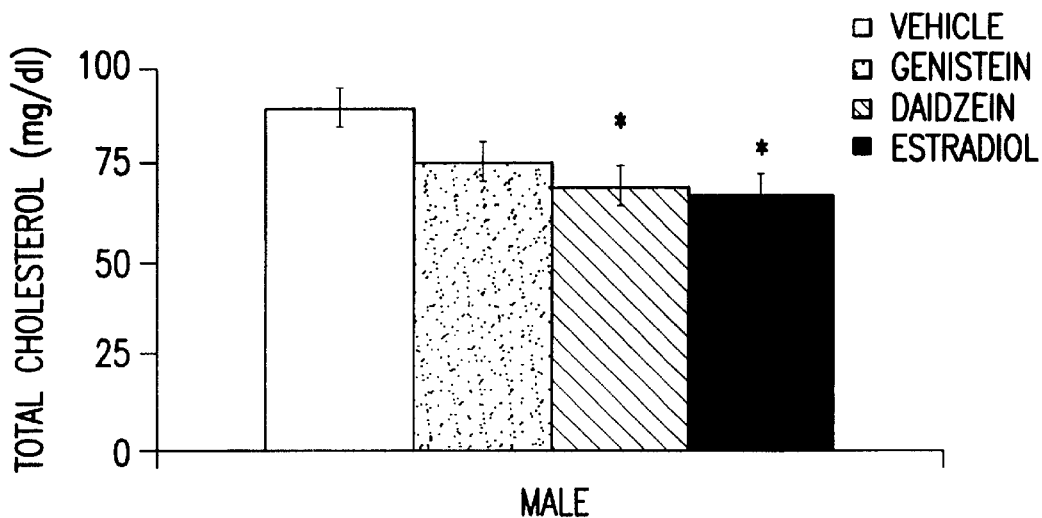
FIG. 6 is a bar graph depicting plasma total cholesterol concentration in male Sprague-Dawley rats injected with vehicle control, genistein, daidzein, or estradiol for 6 weeks.
Figure 7:
FIG. 7 is a bar graph depicting plasma fasting glucose levels in male Sprague-Dawley rats injected with vehicle control, genistein, daidzein, or estradiol for 6 weeks.

[1]Values are means of each injection group.
[2]Injection groups; V, vehicle control; G, genistein; E, estradiol; D, daidzein.
[3]FER = g of weight change/g of food intake.
[a]significantly different (P < .05) vs V
[b]significantly different (P < .05) vs G
[c]significantly different (P < .05) vs D the V group (FIG. 6). There was a non-significant trend (P<0.5) toward lower plasma cholesterol levels in the G treated animals vs the V group (FIG. 6). Additionally, there was a animals vs the V non-significant trend (P<0.1) toward lower blood glucose levels in the E treated group (FIG. 7).

Liver Weight and Lipid Evaluations:

Liver weights were considerably (P<0.05) lower in the D, G, and E treated animals vs the V group (Table 6). Surprisingly, when liver weight as a % of body weight was evaluated, the E treated animals had similar values to the V treated animals; whereas, the D and G groups still demonstrated a reduction in relative liver mass. Liver total cholesterol was significantly (P<0.05) higher in the E treated rats when compared to the V, G, and D animals. Liver cholesteryl esters were significantly (P<0.05) higher in the E treated rats when compared to the V and G treatments. Liver triglyceride concentrations were significantly (P<0.05) lower in the D treatment when compared to the E treatment.

TABLE 6

Liver Cholesterol and Triglyceride Concentrations in Male Sprague-Dawley Rats Injected with Vehicle Control, Genistein, Daidzein, or Estradiol for 6 Weeks[1]

| Injection Group[2] | n | Liver weight g | Unesterified Cholesterol | Cholesteryl esters | Total Cholesterol | Total Triglycerides[3] |
|---|---|---|---|---|---|---|
| | | | μmol/g liver | | | |
| V | 10 | 14.179 | 2.155 | 2.812 | 4.986 | 24.943 |
| G | 9 | 12.970[a] | 2.600 | 2.589 | 5.189 | 29.528 |
| D | 10 | 12.857[a] | 2.563 | 3.114 | 5.678 | 17.980 |
| E | 10 | 10.487[a,b,c] | 2.618 | 4.104[a,b] | 6.722[a,b,c] | 32.186[c] |

Figure 8:
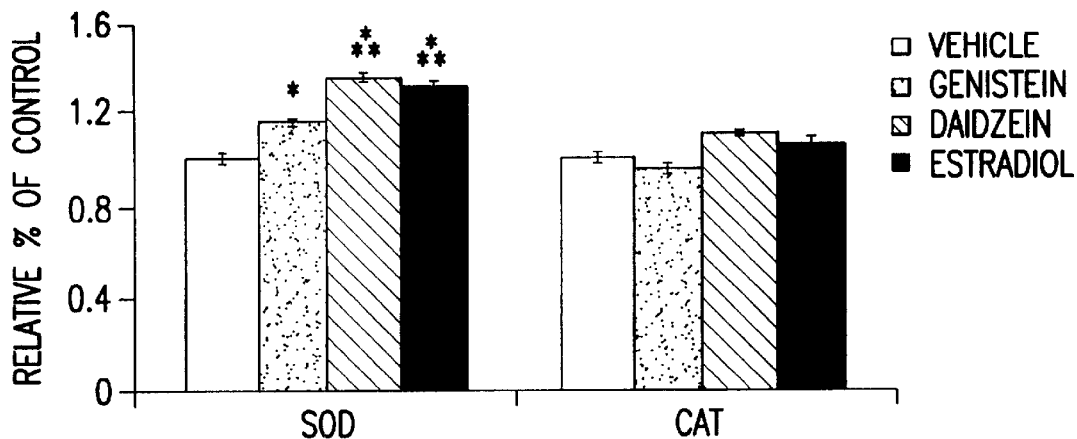
FIG. 8 is a bar graph depicting liver cellular antioxidant levels of superoxide dimutase (SOD) and catalase (CAT) in male Sprague-Dawley rats injected with vehicle control, genistein, daidzein, or estradiol for 6 weeks.

[1]Values are means of each injection group.
[2]Injection groups: V, vehicle control; G, genistein; E, estradiol; D, daidzein.
[3]Total triglycerides as triolein (MW 885.4).
[a]significantly different (P < .05) vs V
[b]significantly different (P < .05) vs G
[c]significantly different (P < .05) vs D Liver Free Radical Scavenger Evaluations:

Subcutaneous injection of estrogenic compounds (i.e. G, D, and E) had a varied effect on the status of antioxidant defense systems tested in these rat livers. The level of catalase did not appear to be effected by treatment with any of these compounds. Means were similar for each group, and differences among them varied by less than 10% (FIG. 8). In contrast, all three treatment groups had significantly higher levels of SOD activity than matched vehicle controls (FIG. 8). Genistein which affected SOD the least of the three treatment groups, raised the activity of this enzyme by 15% (P<0.05). By comparison, daidzein and estradiol, which were of equal effectiveness in these trials, elevated SOD activity over that of controls, both by approximately 33% (P<0.05). In addition to the increases in activity over V rat livers, E and D treatments' elevation of SOD activity was significantly higher than that seen with G treatment (P<0.05).

EXAMPLE V

The Effects of Soy Protein and Soy Isoflavones on Symptoms Associated with Cardiovascular Disease in Rats Animals and Diets.

Thirty male and thirty female Sprague-Dawley rats were randomly assigned to one of three treatment groups: High-Isoflavone (2.39 mg/g protein) Soy Protein (HS); Low Isoflavone (0.11 mg/g protein) Soy Protein (LS)-, or Non-Soy (Casein) Protein (C). All other micro/macro nutrients were held constant in the diets. Following sacrifice, blood was collected for wing insulin and glucose measurements and the abdominal fat pads and reproductive organs were removed and weighed.

Feed and Weight Measurements.

Animal weight and feed intake were measured weekly during the six week study and the subsequent feed-efficiency ratio [FER (g of weight change/g of feed intake)] was determined. Following sacrifice, the abdominal fat pads, liver, and reproductive organs were removed and weighed for comparison.

Plasma Glucose, Cholesterol, and Insulin Analysis.

Collected blood was heparinized and centrifuged, and plasma aliquots were then used for glucose, total cholesterol, and insulin determinations, using standard glucose oxidase (Fisher Scientific, St. Louis, Mo.), cholesterol kits (Fisher Scientific, St. Louis, Mo.), and insulin RIA kits.

Statistical Analysis.

These studies used a randomized design. All data were analyzed by one-way analysis of variance (ANOVA) and post-hoc comparisons were made with Tukev pairwise comparisons test. Significance was confined at P<0.05 (SYSTAT 7.0, SPSS INC., 1997), and all values are reported as means ±standard error of the mean.

Results.

Figure 9:
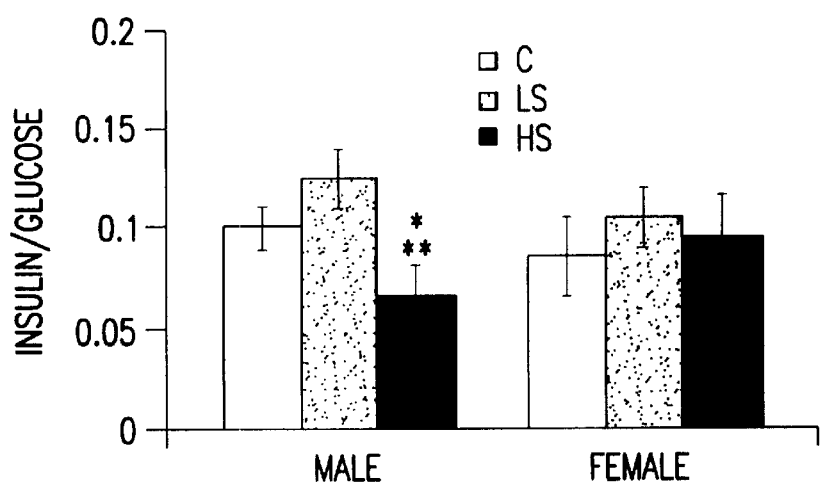
FIG. 9 is a bar graph depicting insulin to glucose ratio in male and female Sprague-Dawley rats fed high-isoflavone soy protein (HS), low-isoflavone soy protein (LS), or non-soy (casein) protein (C) for 6 weeks.

In the male rats fed LS and HS, there was a marked (P<0.05) reduction in body and intra-abdominal fat weight when compared to C. There was no difference in gonadal weight between any of the male groups. The male HS rats had a reduction in FER, insulin, and insulin to glucose ratios (I/G) ratio (FIG. 9) vs. C. In addition, the male HS rats also demonstrated a non-significant trend (P<0.1) toward a reduction in plasma total cholesterol when compared to the C animals. The gross physiological and metabolic effects in the male rats were not manifested in the female rats. Moreover, the female LS rats had an increase (P<0.05) in Intraabdominal fat vs. C and the female HS rats had an increase (P<0.05) in plasma glucose vs. C.

EXAMPLE VI

High Isoflavone Soy Protein Ameliorates Impaired Glucose Tolerance and Fatty Liver in Female Zucker Obese Rats Materials and Methods.

Female obese Zucker rats were assigned to one of three diet groups: High-Isoflavone Soy Protein (HIS); Low- Isoflavone Soy Protein (LIS); or Non-Soy (Casein) Protein (C) diets. During the 10-week study, body weight, feed intake and feed efficiency ratio (FER) were assessed. Additionally, a Glucose Tolerance Test was performed and plasma, abdominal fat pads, liver and reproductive organs were collected, weighed and frozen for subsequent analysis. Results.

Figure 10:
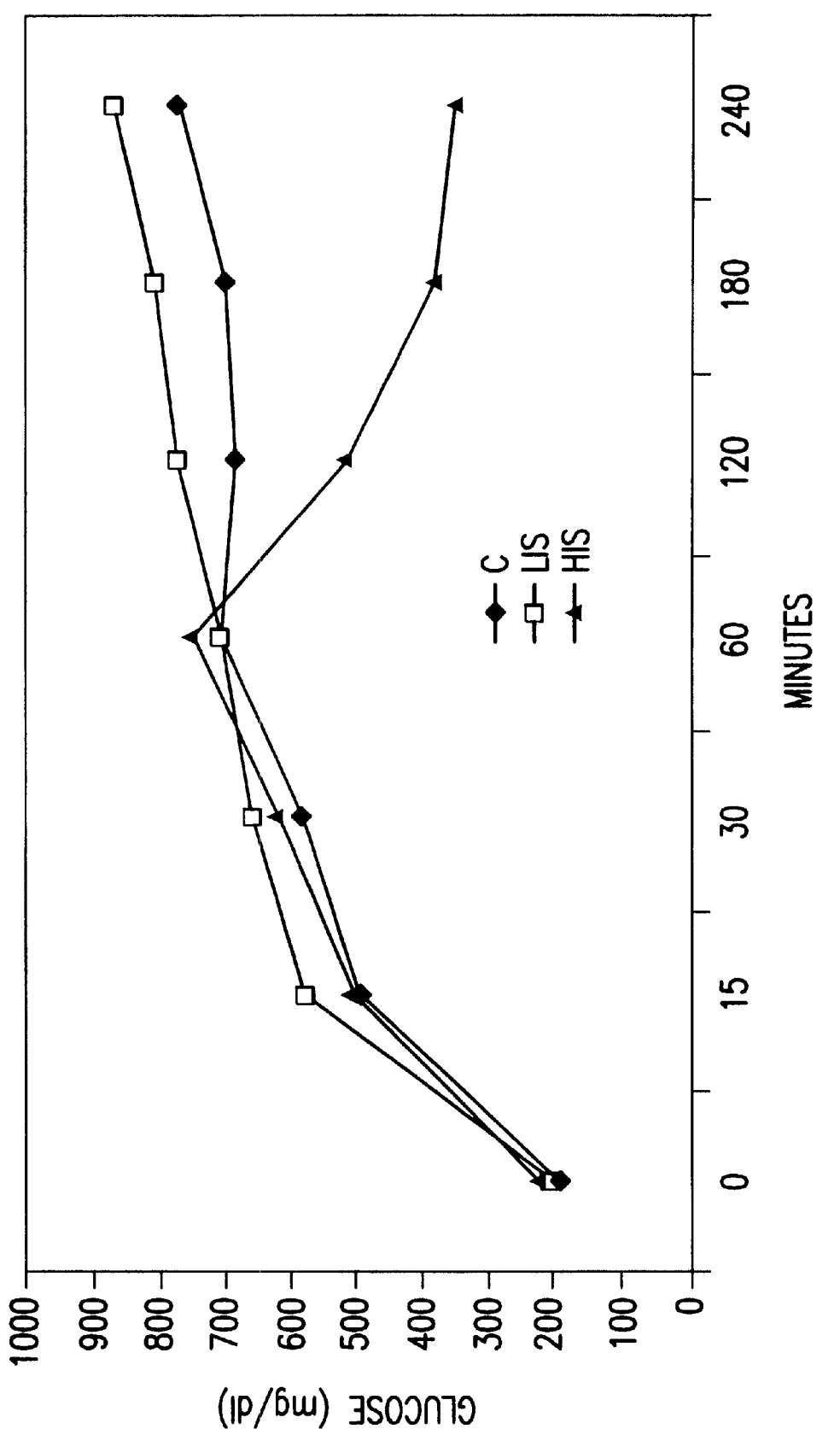
FIG. 10 is a graph depicting glucose tolerance test (GTT) in female obese Zucker rats.
Figure 11:
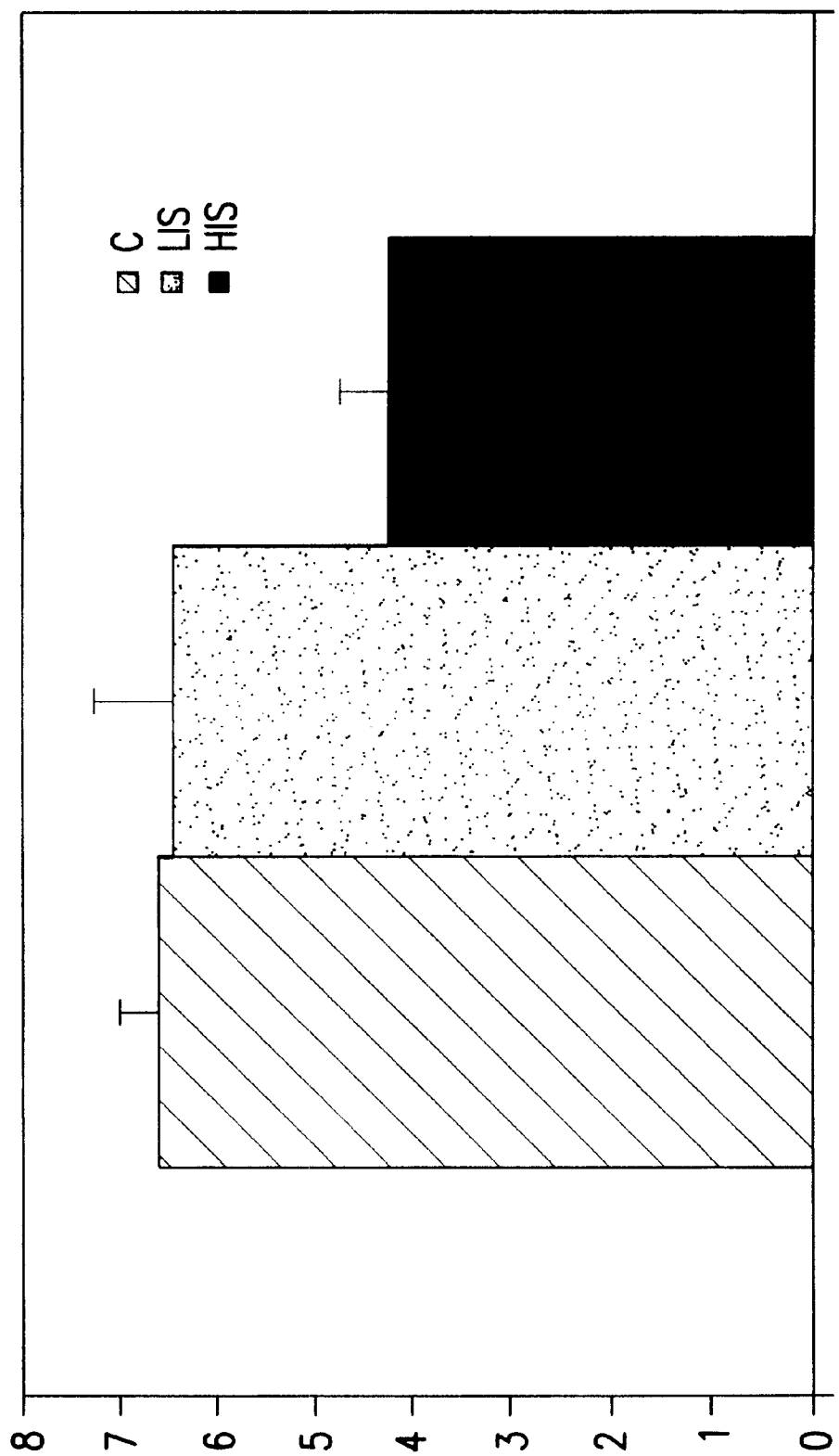
FIG. 11 is a bar graph depicting liver weight in female obese Zucker rats.
Figure 12:
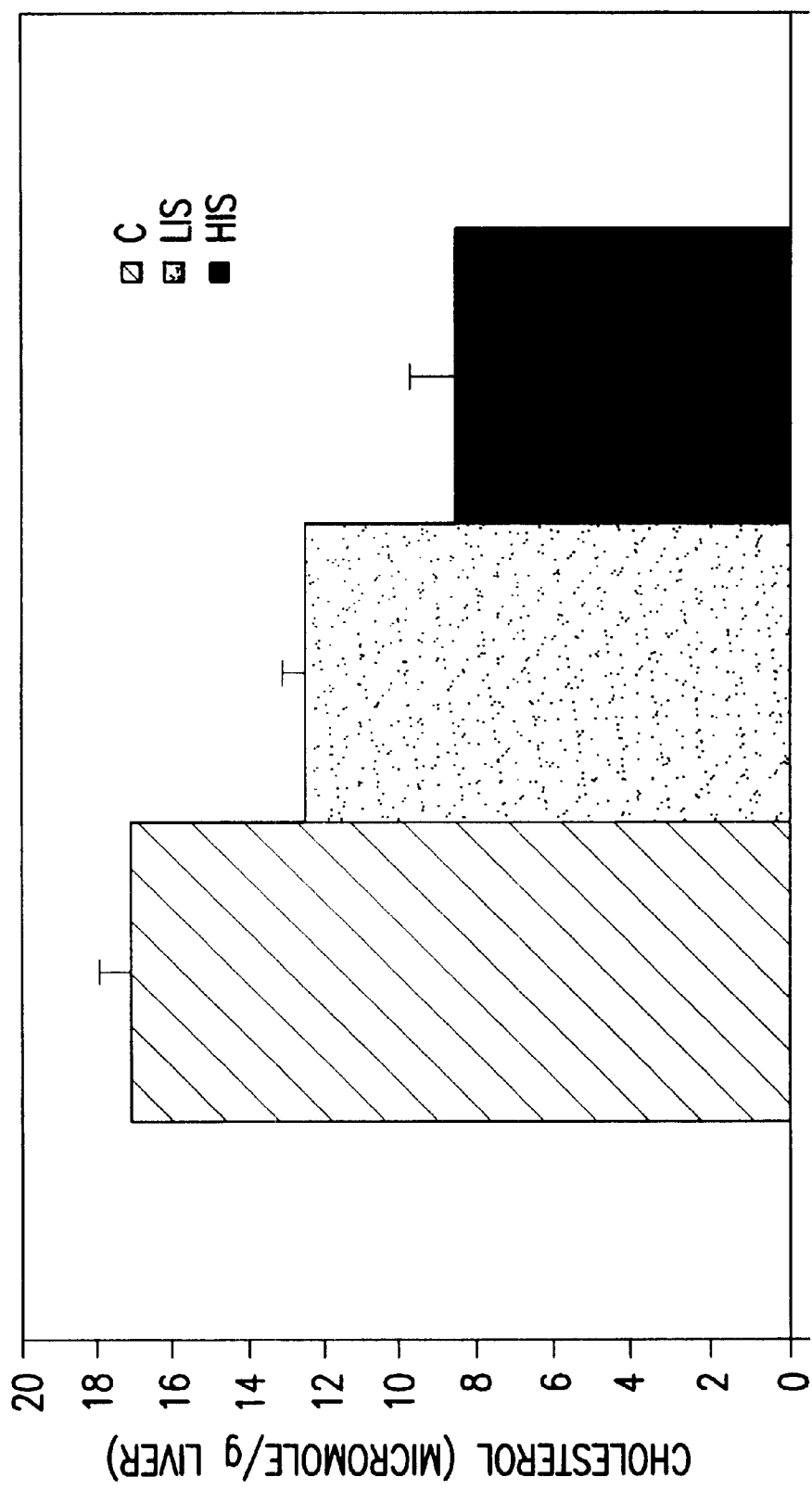
FIG. 12 is a bar graph depicting liver cholesterol in female obese Zucker rats.
Figure 13:
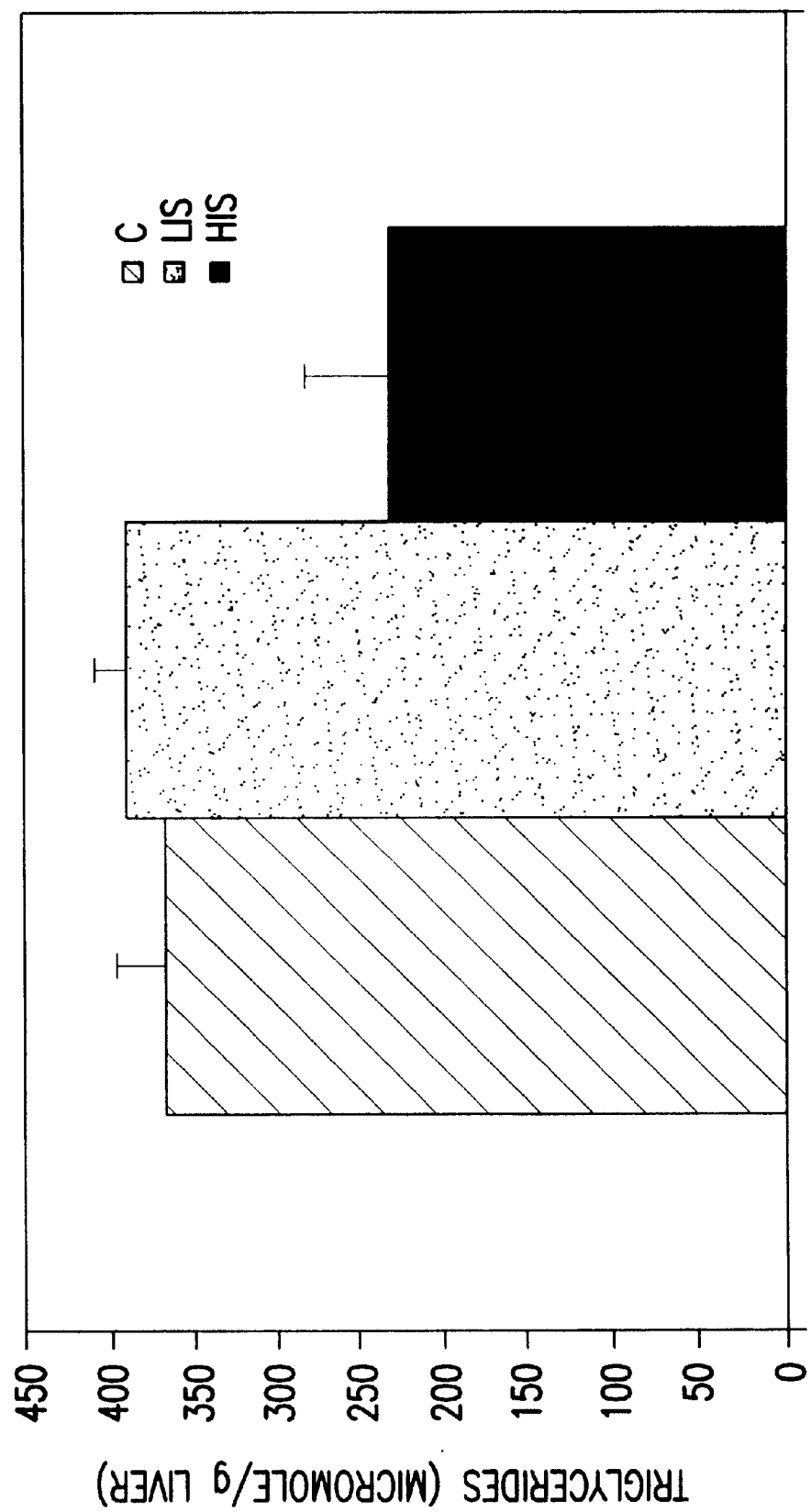
FIG. 13 is a bar graph depicting liver triglycerides in female obese Zucker rats.
Figure 14:
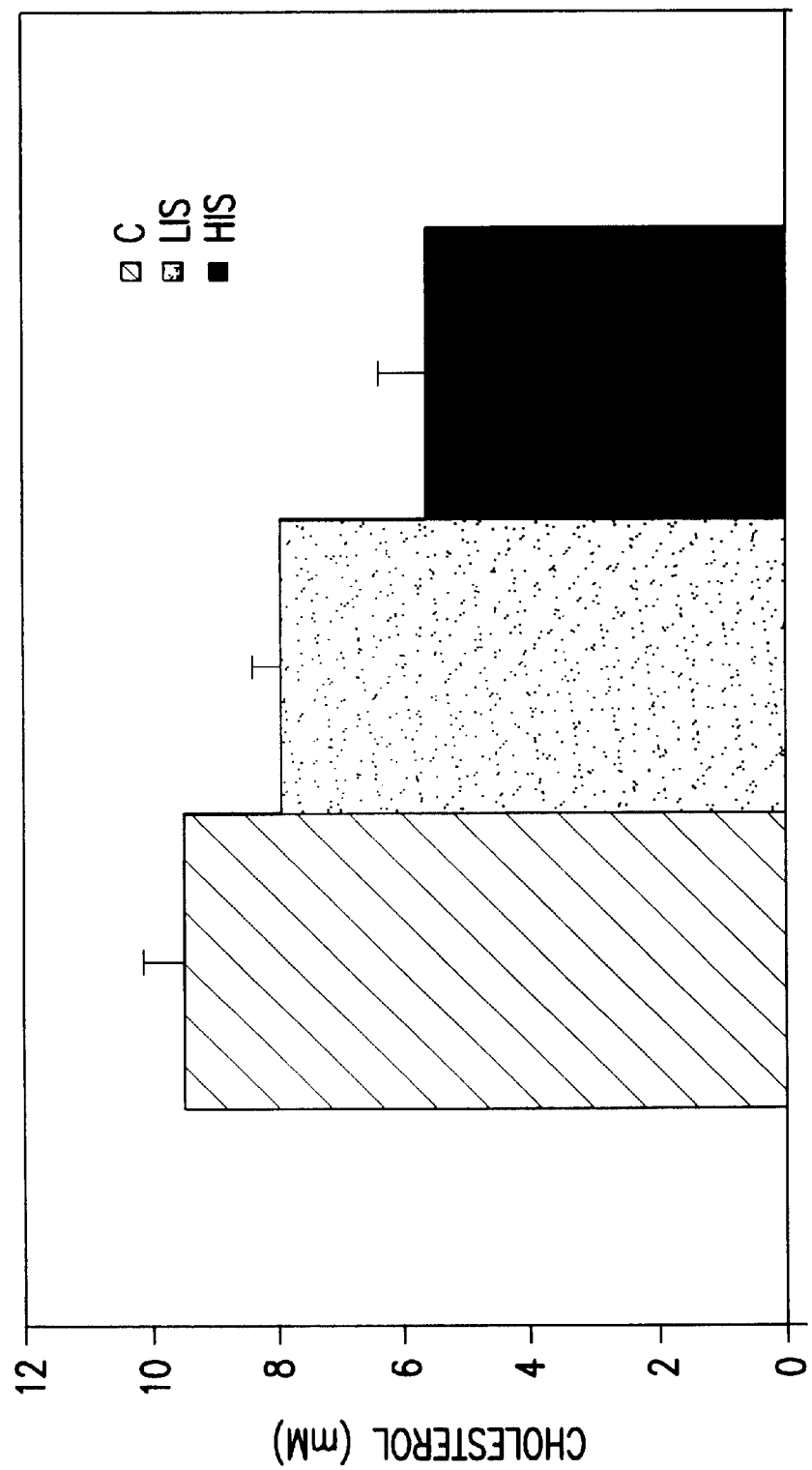
FIG. 14 is a bar graph depicting plasma total cholesterol in female obese Zucker rats.

The High-Isoflavone Soy Protein (HIS) diet significantly ($P<0.05$) improved glucose tolerance (FIG. 10), fatty liver (i.e. decreased liver weight, liver cholesterol, and liver triglycerides) (FIGS. 11–13), and plasma cholesterol (FIG. 14) relative to the Low-Isoflavone Soy Protein (LIS) and Non-Soy (Casein) Protein (C) diets.

It will be clear that the invention can be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. A method for treating a condition selected from the group consisting of hepatic steatosis and steatohepatitis, said method comprising administering to a subject having said condition an effective amount of at least one isolated isoflavonoid selected from the group consisting of genistein, genisitin, 6"-O-malonylgenistin, 6"-O-acetyl genistin, daidzein, daidzin, 6"-O-malonyldaidzin, 6"-O-acetyldaidzin, glycitein, glycitin, 6"-O-malyonylglycitin, 6"-O-acetylglycitin, biochanin A, formononetin and mixtures thereof.

2. The method of claim 1 wherein said at least one isolated isoflavonoid is derived from soy bean.

3. The method of claim 1 wherein said at least one isolated isoflavonoid is administered in combination with at least one dietary ingredient or supplement other than soy protein.

4. The method of claim 1 wherein said at least one isolated isoflavonoid is administered in combination with a saponin.

5. The method of claim 1, wherein said at least one isolated isoflavonoid is genistein.

6. The method of claim 1, wherein said at least one isolated isoflavonoid is genistin.

7. The method of claim 1, wherein said at least one isolated isoflavonoid is 6"-O-malonylgenistin.

8. The method of claim 1, wherein said at least one isolated isoflavonoid is 6"-O-acetylgenistin.

9. The method of claim 1, wherein said at least one isolated isoflavonoid is daidzein.

10. The method of claim 1, wherein said at least one isolated isoflavonoid is daidzin.

11. The method of claim 1, wherein said at least one isolated isoflavonoid is 6"-O-malonyldaidzin.

12. The method of claim 1, wherein said at least one isolated isoflavonoid is 6"-O-acetyldaidzin.

13. The method of claim 1, wherein said at least one isolated isoflavonoid is glycitein.

14. The method of claim 1, wherein said at least one isolated isoflavonoid is glycitin.

15. The method of claim 1, wherein said at least one isolated isoflavonoid is 6"-O-malonylglycitn.

16. The method of claim 1, wherein said at least one isolated isoflavonoid is 6"-O-acetylglycitin.

17. A method for reducing liver weight in a subject suffering from hepatic steatosis, said method comprising administering to the subject an effective amount of at least one isolated isoflavonoid selected from the group consisting of genistein, genisitin, 6"-O-malonylgenistin, 6"-O-acetyl genistin; daidzein, daidzin, 6"-O-malonyldaidzin, 6"-O-acetyldaidzin, glycitein, glycitin, 6"-O-malyonylglycitin, 6"-O-acetylglycitin, biochanin A, formononetin and mixtures thereof.

18. The method of claim 17, wherein said at least one isolated isoflavonoid is genistein.

19. The method of claim 17, wherein said at least one isolated isoflavonoid is genistin.

20. The method of claim 17, wherein said at least one isolated isoflavonoid is 6"-O-malonylgenistin.

21. The method of claim 17, wherein said at least one isolated isoflavonoid is 6"-O-acetylgenistin.

22. The method of claim 17, wherein said at least one isolated isoflavonoid is daidzein.

23. The method of claim 17, wherein said at least one isolated isoflavonoid is daidzin.

24. The method of claim 17, wherein said at least one isolated isoflavonoid is 6"-O-malonyldaidzin.

25. The method of claim 17, wherein said at least one isolated isoflavonoid is 6"-O-acetyldaidzin.

26. The method of claim 17, wherein said at least one isolated isoflavonoid is glycitein.

27. The method of claim 17, wherein said at least one isolated isoflavonoid is glycitin.

28. The method of claim 17, wherein said at least one isolated isoflavonoid is 6"-O-malonylglyctin.

29. The method of claim 17, wherein said at least one isolated isoflavonoid is 6"-O-acetylglytin.

* * * * *

UNITED STATES PATENT AND TRADEMARK OFFICE
CERTIFICATE OF CORRECTION

PATENT NO. : 6,592,910 B1
DATED : July 15, 2003
INVENTOR(S) : Banz et al.

It is certified that error appears in the above-identified patent and that said Letters Patent is hereby corrected as shown below:

<u>Title page,</u>
Item [56], References Cited, OTHER PUBLICATIONS, please delete "Banz, W. et al. 'The Effects of Soy Protein and Isoflavones on Platelet, Lipid and Liver Measurements in Zucker Rats,' *FASEB J.* 13: A885 (Mar. 1999)." and insert therefore -- Banz, W. et al., "The Effects of Soy Protein and Isoflavones on Platelet, Lipid and Liver Measurements in Zucker Rats," *FASEB J.* 13: A885 (Apr. 1999). --; and please delete "Banz, W. et al. 'High Isoflavone Soy Protein Ameliorates Impaired Glucose Tolerance and Fatty Liver in Female Zucker Obese Rats' *FASEB J.* 14:A765 (Mar. 2000)." and insert therefor -- Banz, W. et al., "High Isoflavone Soy Protein Ameliorates Impaired Glucose Tolerance and Fatty Liver in Female Zucker Obese Rats", *FASEB J.* 14:A765 (Apr. 2000). --.

Signed and Sealed this

Thirteenth Day of April, 2004

JON W. DUDAS
*Acting Director of the United States Patent and Trademark Office*